US011085074B2

(12) United States Patent
Keys et al.

(10) Patent No.: US 11,085,074 B2
(45) Date of Patent: Aug. 10, 2021

(54) SYSTEMS AND METHODS FOR PERFORMING DIGITAL PCR

(71) Applicant: LIFE TECHNOLOGIES CORPORATION, Carlsbad, CA (US)

(72) Inventors: David N. Keys, Alameda, CA (US); Nivedita Sumi Majumdar, San Bruno, CA (US); Theodore E. Straub, Lexington, MA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 264 days.

(21) Appl. No.: 15/280,160

(22) Filed: Sep. 29, 2016

(65) Prior Publication Data

US 2017/0088879 A1  Mar. 30, 2017

Related U.S. Application Data

(60) Provisional application No. 62/234,158, filed on Sep. 29, 2015.

(51) Int. Cl.
*C12Q 1/686* (2018.01)
*C12Q 1/6851* (2018.01)
*B01L 7/00* (2006.01)

(52) U.S. Cl.
CPC ............ *C12Q 1/686* (2013.01); *C12Q 1/6851* (2013.01); *B01L 7/52* (2013.01); *B01L 2300/024* (2013.01); *B01L 2300/0829* (2013.01)

(58) Field of Classification Search
None
See application file for complete search history.

(56) References Cited

U.S. PATENT DOCUMENTS

| | | | | |
|---|---|---|---|---|
| 2006/0008809 | A1* | 1/2006 | Li | C12Q 1/6851 435/6.12 |
| 2007/0026421 | A1* | 2/2007 | Sundberg | B01L 7/525 435/6.12 |
| 2010/0092973 | A1* | 4/2010 | Davies | B01L 7/525 435/6.19 |
| 2010/0120032 | A1* | 5/2010 | Van Den Bulcke | C12Q 1/6844 435/6.12 |
| 2014/0045712 | A1* | 2/2014 | Link | C12Q 1/686 506/9 |
| 2014/0178889 | A1* | 6/2014 | Do | C12Q 1/686 435/6.12 |
| 2017/0081712 | A1* | 3/2017 | Li | C12Q 1/6837 |

FOREIGN PATENT DOCUMENTS

| | | |
|---|---|---|
| EP | 0487218 | 5/1992 |
| WO | 2008/107014 | 9/2008 |
| WO | 2011/143478 | 11/2011 |
| WO | 203/158982 | 10/2013 |

OTHER PUBLICATIONS

Fraley et al. (2013). Universal digital high-resolution melt: a novel approach to broad based profiling of heterogeneous biological samples. Nucleic Acids Research, vol. 41(18) e175, p. 1-13.*
Rasmussen et al. Quantitative PCR by Continuous Fluorescence Monitoring of a Double Strand DNA Specific Binding Dye. Biochemica 2:8-11. (Year: 1998).*
Van Poucke et al. Combined FAM-labeled TaqMan probe detection and SYBR green I melting curve analysis in multiprobe qPCR genotyping assays. BioTechniques 52(2):81-85. (Year: 2012).*
Tellinghuisen, J. Absolute Copy Number from the Statistics of the Quantification Cycle in Replicate Quantitative Polymerase Chain Reaction Experiments. Anal. Chem. 87:1889-1895. (Year: 2015).*
HRM Experiments Using MeltDoctor HRM Reagents and High Resolution Melt Software v3.0, User Guide, pp. 1-116, 2010.
International Search Report and Written Opinion for Application No. PCT/US2016/054406 dated Dec. 13, 2016.

* cited by examiner

*Primary Examiner* — Samuel C Woolwine
(74) *Attorney, Agent, or Firm* — David Weber; Michael Mauriel

(57) ABSTRACT

Systems and methods are described for quantifying a target nucleic acid. A sample comprising a target nucleic acid is segregated into a first plurality of the reaction volumes containing at least one target nucleic acid molecule and a second plurality of the reaction volumes containing no target nucleic acid molecules. The reaction volumes are subjected to an amplification assay, wherein the amplification assay is configured to amplify the target nucleic acid. An indicator of amplification is detected or measured in at least some of the plurality of reaction volumes. The target nucleic acid is quantified based on the detection or measurement. After discontinuing the amplification assay, the plurality of reaction volumes may be heated and changes in the indicators of amplification of two or more of the at least some of the reaction volumes may be detected or measured.

5 Claims, 18 Drawing Sheets

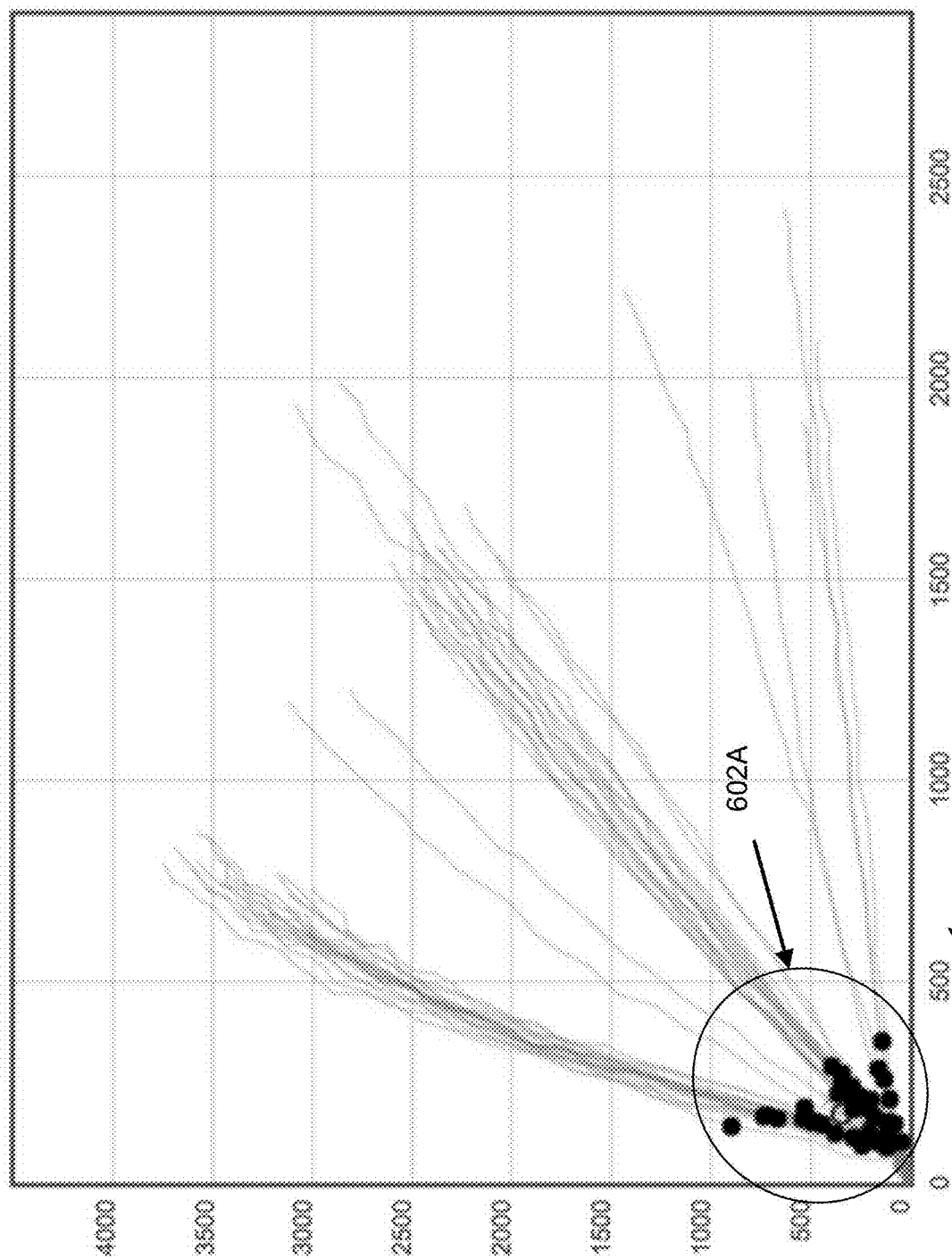

SYSTEMS AND METHODS FOR PERFORMING DIGITAL PCR

CROSS-REFERENCE TO RELATED APPLICATIONS

This application claims the benefit of priority of U.S. Provisional Patent Application No. 62/234,158, filed on Sep. 29, 2015, which is incorporated herein in its entirety by reference.

INTRODUCTION

Digital PCR (dPCR) is a refinement of conventional polymerase chain reaction (PCR) methods which can be used to directly quantify and clonally amplify nucleic acids (including DNA, cDNA, methylated DNA, RNA, or the like). One difference between dPCR and traditional PCR lays in the method of measuring nucleic acids amounts. In dPCR, a sample is separated into a large number of individual sample volumes or portions and respective PCR reactions are carried out in each sample portion individually. This separation allows for sensitive measurement of very small amounts of a nucleic acid. dPCR has been demonstrated as useful for studying variations in gene sequences, such as copy number variation or point mutations.

In dPCR, a sample is partitioned so that individual nucleic acid molecules to be assessed within the sample are localized and concentrated within many separate regions. While the starting number of copies of a molecule is proportional to the number of amplification cycles in conventional PCR, dPCR does not dependent determining a number of amplification cycles to determine the initial sample amount. Instead, the initial sample is partitioned into a large number of relatively small sample portions containing one copy, or approximately one copy, or no copy of the nucleic acid template or target. As a result, each partitioned sample portion may be characterized as a "0" or "1" for containing at least one of a type of target nucleic acid molecule, resulting in a negative ("0") or positive ("1") PCR reaction, respectively. The partitioning of the sample in this way may use Poisson statistics to provide an estimate of molecules in the initial sample. However, the accuracy of this estimate varies, depending on the number of "0" and "1" produced.

There exists a need to improve upon the information and data obtained during dPCR, and the analysis based upon such information, so as to enhance the accuracy of the results obtained from dPCR. For instance, techniques for differentiating between partitioned samples that initially include a single sample cell and those containing more than one sample cell may provide more accurate dPCR results.

SUMMARY

Embodiments of the present invention are generally directed to systems and methods for quantifying one or more nucleic acids. In certain embodiments, a sample or reaction solution is segregated, distributed, or divided into a plurality of sample reaction volumes or reaction sites associated with a sample reaction device, fluidic device, sample holder, or other such device. The plurality of sample reaction volumes may include a first plurality of the sample reaction volumes or reaction sites each containing one molecule, or approximately one molecule, of a target nucleic acid and a second plurality of the sample reaction volumes each containing no molecules of the target nucleic acid. The plurality of sample reaction volumes or reaction sites are subjected to an amplification assay using, for example, at least a primer and a probe or indicator dye, wherein the amplification assay is configured to amplify the target nucleic acid. An indicator of amplification presented by the target nucleic acid present in any of the plurality of sample reaction volumes may be detected or measured during the amplification assay. After the amplification assay is discontinued, the plurality of sample reaction volumes may be further processed, for example, by heating the sample reaction volumes and detecting or measuring changes in the indicator from the reaction volumes. In some embodiments, the indicator may also be detected or measured during one or more cycles of the amplification assay. A sample reaction volume may include a segregated sample (e.g., nucleic acid sample) and one or more reagents for supporting an amplification reaction. The one or more reagents may be incorporated into the sample either before or after loading the sample into the reaction volumes or reaction sites.

In certain embodiments, after the amplification assay is completed, a first detection or measurement may be taken of an indicator of amplification at a first temperature for at least some of the plurality of the sample reaction volumes, wherein the indicator provides an indication of the existence and/or amount of the amplified product. Optionally, one or more additional detections or measurements of the indicator may be taken after the amplification assay is completed at one or more additional temperatures that are different than the first temperature, for example, at one or more temperatures that are higher than the first temperature. Optionally, one or more detections or measurements of the indicator may also be taken during one or more cycles of the amplification assay, for example, at a same predetermined assay temperature in two or more cycles of the amplification, wherein the assay temperature may be higher than the first temperature.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation.

FIGS. 6A and 6B illustrate a graph of illustrative, prophetic exemplary real time amplification detection measurements with angle of launch depictions.

DETAILED DESCRIPTION

Figure 1A:
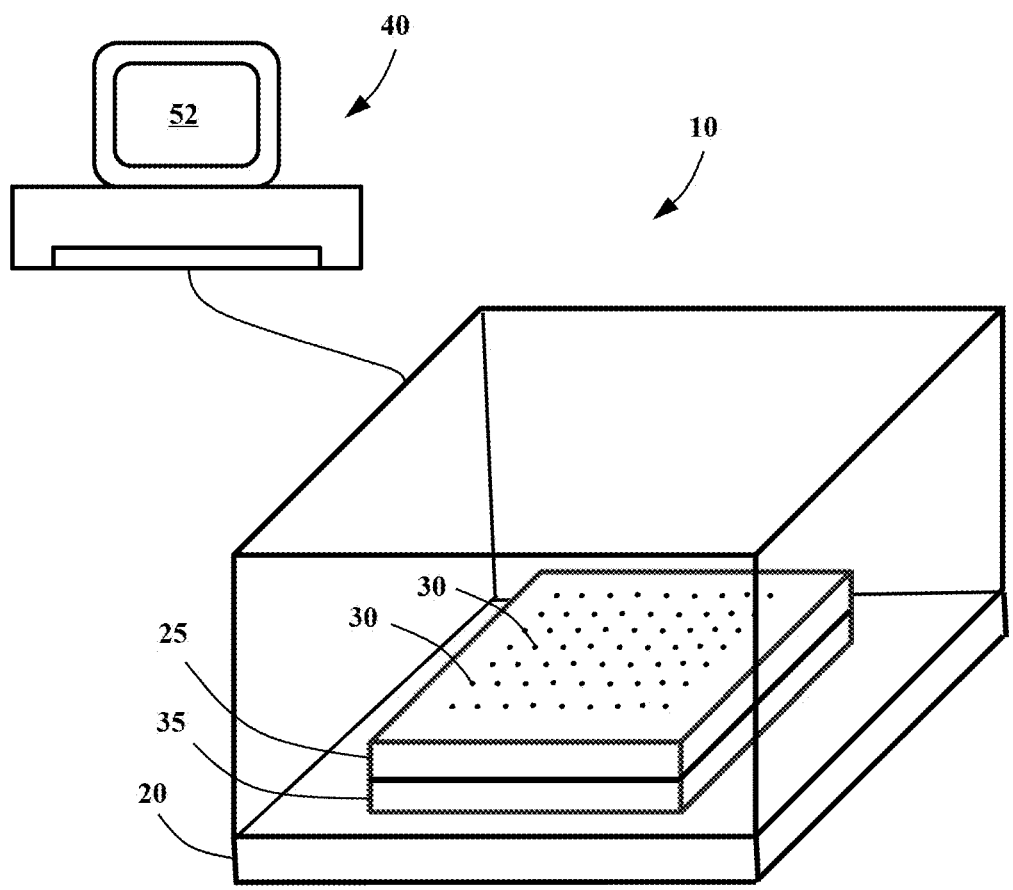
FIG. 1A illustrates a system according to an embodiment of the present invention.

This description and the accompanying drawings that illustrate exemplary embodiments should not be taken as limiting. Various mechanical, compositional, structural, electrical, and operational changes may be made without departing from the scope of this description and claims, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

As used herein, the term "biological sample" or "sample" means a material, substance, or solution comprising one or more biological molecules, chemicals, components, and/or compounds (e.g., a nucleic acid, DNA molecule, or RNA molecule) of interest to a user, manufacturer, or distributor of the various embodiments of the present invention described or implied herein. A sample may include, but is not limited to, one or more of a DNA sequence (including cell-free DNA), an RNA sequence, a gene, an oligonucleotide, an amino acid sequence, a protein, a biomarker, or a cell (e.g., circulating tumor cell), or any other suitable target biomolecule. As used herein, the term "sample solution" means a liquid or fluid comprising at least one sample.

As used herein, the term "reagent" means a material or substance (e.g., in solid and/or liquid form) containing chemicals or compounds to be used in combination with a sample in order to facilitate a biological assay, test, process, or experiment (e.g., a PCR assay, test, process, or experiment). A reagent may comprise a combination of at least one nucleotide, at least one oligonucleotides, at least one primer, at least one polymerase, at least one salt, at least one buffering agent, at least one dye (e.g., control dye and/or binding dye), at least one marker, at least one probe, at least one enhancing agent, at least one enzyme, at least one detergent, and/or at least one blocking agent. The reagent may comprise at least one master mix (MMx) containing, for example, a combination of at least one polymerase, at least one nucleotide, at least one salt, at least one buffering agent, at least one dye (e.g., control dye and/or binding dye), and/or at least one enhancing agent. In some cases, the MMx may include one or more DNA binding dyes (e.g., a SYBR dye) or other chemicals.

As used herein, the term "reaction solution", "reaction mix", and "reaction build" means a solution or mixture containing both a biological sample and one or more reagents. The reaction solution, reaction mix, or reaction build may be used in conjunction with one or more of PCR (e.g., qPCR, dPCR, multiplex dPCR), fetal diagnostics, viral detection, quantification standards, genotyping, sequencing, sequencing validation, mutation detection, detection of genetically modified organisms, rare allele detection, and/or copy number variation, or the like.

As used herein, an "indicator" means a physical, electrical, magnetic, chemical, and/or optical property or effect produced by a sample that may be used in determining the existence and/or in determining, measuring, or estimating the amount of a target nucleic acid. An indicator may comprise one or more of luminescence (e.g., fluorescence, chemiluminescence, bioluminescence), color, transmissivity, opacity, reflectivity, or polarization, pH, charge, surface potential, current, or voltage changes.

As used herein, the term "amplification product" means any product produced by an amplification assay or process, for example, an increased number of target nucleic acid molecules or other nucleic acid molecules produced during a PCR assay or process (e.g., during a qPCR or dPCR assay or process). As used herein, an "indicator of amplification" means a physical, electrical, magnetic, chemical, and/or optical property or effect produced by a sample that may be used in determining the existence, and/or in determining, measuring, or estimating an amount of amplification of a target nucleic acid in a biological assay, test, process, or experiment (e.g., a PCR assay, test, process, or experiment). An indicator of amplification may comprise one or more of luminescence (e.g., fluorescence, chemiluminescence, bioluminescence), color, transmissivity, opacity, reflectivity, or polarization, pH, charge, surface potential, current, or voltage changes.

Polymerase chain reaction (PCR) may comprise a thermal cycling process, in which cycles of heating and cooling are used to provide repeated cycles of nucleic acid melting and enzymatic replication of nucleic acids. A number of PCR methods use thermal cycling involving alternately heating and cooling the PCR sample to a defined series of temperature steps. These thermal cycling steps may be used first to physically separate nucleic acids, such as separating the two strands in a nucleic acid double helix, at a high temperature in a process called melting. At a lower temperature, each strand is then used as the template in synthesis by the polymerase to selectively amplify a target nucleic acid during an annealing phase and extension phases. Example polymerases include heat-stable polymerase such as, for example, Taq polymerase. The selectivity of PCR results from the use of primers that are complementary to nucleic acid regions targeted for amplification under specific thermal cycling conditions. Primers (short nucleic acid fragments) containing sequences complementary to the target region along with a polymerase, are used to enable selective and repeated amplification.

Referring to FIG. 1A, in certain embodiments of the present invention, a system or instrument 10 for detecting or quantifying a nucleic acid in a sample or sample solution comprises base and/or housing 20. The base and/or housing 20 comprises, or is configured to receive, contain, or hold, a reaction device 25. The reaction device 25 comprises, or is configured to provide, a plurality of sample reaction volumes 30 receiving, containing, holding, and/or segregating all or a portion of the sample or sample solution. Optionally, the system 10 may additionally comprise a temperature controller 35 such as a thermal cycler, or the like (e.g., for performing a qPCR assay).

Figure 10:
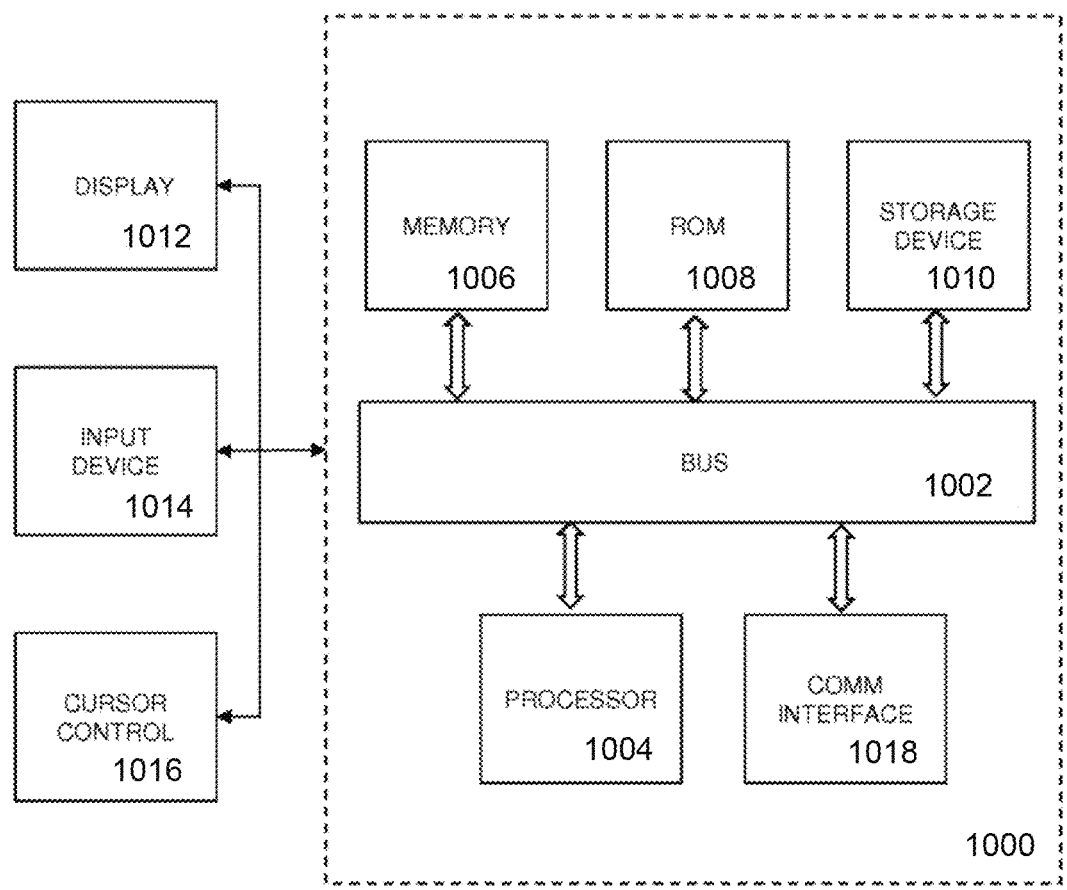
FIG. 10 illustrates a block diagram of a computer system in accordance with various embodiments described herein.

With additional reference to FIG. 10, the system 10 may also comprise computer system 1000. The computer system 1000 may be configured or employed to carry out processing functionality, according to various embodiments, upon which embodiments of temperature controller 35 may be utilize, when present. Computing system 1000 can include one or more processors, such as a processor or electronic processor 1004. Processor 1004 can be implemented using a general or special purpose processing engine such as, for example, a microprocessor, controller or other control logic.

In certain embodiments, a digital amplification technique is performed. For example, the digital amplification technique may comprise a digital PCR (dPCR) assay, process, experiment, or test, wherein a sample or reaction solution is segregated, distributed, or divided, into a plurality of sample reaction volumes or reaction sites associated with a reaction device, fluidic device, sample holder, or other such device. The plurality of sample reaction volumes may include a first plurality of the sample reaction volumes each containing one molecule or approximately one molecule of a target nucleic acid and a second plurality of the sample reaction volumes each containing no molecules of the target nucleic acid. The plurality of sample reaction volumes or reaction sites are subjected to an amplification assay using, for example, at least a primer and probe or indicator dye, wherein the amplification assay is configured to amplify the target nucleic acid. During the dPCR assay, an indicator of the target present in any of the plurality of sample reaction volumes may be detected or measured. Similar to other types of PCR, dPCR may progress by exposing the partitioned sample reaction volumes, which contain reagents for amplification, to an amplification assay designed to amplify the target nucleic acid. For example, thermal cycling may be performed such that the template nucleic acid is amplified within the reaction volumes that include an initial one, or approximately one, copy of the template nucleic acid molecule.

In order to quantify the nucleic acid amplification, an indicator of amplification exhibited by the reaction volumes may be detected. In some exemplary embodiments in accordance with the present disclosure, one or more fluorescent dyes or probes may be used such that the dyes or probes bond to nucleic acids and exhibit fluorescence to indicate presence of a nucleic acid.

For example, amplified target nucleic acids can be detected using a detectable nucleic acid binding agent which can be, for example, an intercalating agent or a non-intercalating agent. As used herein, an intercalating agent is an agent or moiety capable of non-covalent insertion between stacked base pairs of a double-stranded nucleic acid molecule. A non-intercalating agent is one that does not insert into the double-stranded nucleic acid molecule. The nucleic acid binding agent can produce a detectable signal directly or indirectly. The signal can be detectable directly using, for example, fluorescence or absorbance, or indirectly using, for example, any moiety or ligand that is detectably affected by its proximity to double-stranded nucleic acid is suitable, for example a substituted label moiety or binding ligand attached to the nucleic acid binding agent. It is typical for the nucleic acid binding agent to produce a detectable signal when bound to a double-stranded nucleic acid that is distinguishable from the signal produced when that same agent is in solution or bound to a single-stranded nucleic acid. For example, intercalating agents such as ethidium bromide fluoresce more intensely when intercalated into double-stranded DNA than when bound to single-stranded DNA, RNA, or in solution (see, e.g., U.S. Pat. Nos. 5,994,056; 6,171,785; and 6,814,934). Similarly, actinomycin D fluoresces red when bound to single-stranded nucleic acids, and green when bound to double-stranded nucleic acids. And in another example, the photoreactive psoralen 4-aminomethyle-4-5',8-trimethylpsoralen (AMT) has been reported to exhibit decreased absorption at long wavelengths and fluorescence upon intercalation into double-stranded DNA (Johnston et al. Photochem. Photobiol. 33:785-791 (1981). For example, U.S. Pat. No. 4,257,774 describes the direct binding of fluorescent intercalators to DNA (e.g., ethidium salts, daunomycin, mepacrine and acridine orange, 4',6-diamidino-α-phenylindole). Non-intercalating agents (e.g., minor groove binders such as Hoechst 33258, distamycin, netropsin) may also be suitable for use. For example, Hoechst 33258 (Searle, et al. Nucleic Acids Res. 18:3753-3762 (1990)) exhibits altered fluorescence with an increasing amount of target. Exemplary detectable DNA binding agents may include, for example, acridine derivatives (e.g., acridine homodimer, acridine orange, acridine yellow, 9-amino-6-chloro-2-methoxyacridine (ACMA), proflavin,), actinomycins (e.g., actinomycin D (Jain, et al. J. Mol. Biol. 68:1-10 (1972), 7-amino-actinomycin D (7-AAD)), anthramycin, auramine, azure B, BOBO™-1, BOBO™-3, BO-PRO™-1, BO-PRO™-3, chromomycin (e.g., A3), crystal violet, cyanine dyes, DAPI (Kapúsciński, et al. Nucleic Acids Res. 6:3519-3534 (1979)), 4',6-diamidino-2-phenylindole (DAPI), daunomycin, distamycin (e.g., distamycin D), dyes described in U.S. Pat. No. 7,387,887, ellipticine, ethidium salts (e.g., ethidium bromide, ethidium homdimer-1, ethidium homdimer-2, dihydroethidium (also known as hydroethidine), ethidium monoazide), fluorcoumanin, fluorescent intercalators as described in U.S. Pat. No. 4,257,774, GelStar® (Cambrex Bio Science Rockland Inc., Rockland, Me.), hexidium iodide, Hoechst 33258 (Searle, et al., (supra)), Hoechst 33342, Hoechst 34580, homidium, hydroxystilbamidine, JO-JO-1, JO-PRO™-1, LDS 751, LOLO-1, LO-PRO™-1, malachite green, mepacrine (e.g., orange), mithramycin, netropsin, the Nissl substance, 4′,6-diamidino-α-phenylindole, proflavine, POPO™-1, POPO™-3 PO-PRO™-1, propidium iodide, ruthenium polypyridyls, Sevron dyes (e.g., Brilliant Red 2B, Brilliant Red 4G, Brilliant Red B, Orange, Yellow L), SYBR 101, SYBR 102, SYBER 103, SYBR® Gold, SYBR® Green I (U.S. Pat. Nos. 5,436,134 and 5,658,751), SYBR® Green II, SYTOX® Blue, SYTOX® Green, SYTOX® Orange, SYTO® 1, SYTO® 11, SYTO® 13, SYTO® 14, SYTO® 15, SYTO® 16, SYTO® 17, SYTO® 18, SYTO® 20, SYTO® 21, SYTO® 22, SYTO® 23, SYTO® 24, SYTO® 25, SYTO® 40, SYTO® 43, SYTO® 44, SYTO® 45, SYTO® 59, SYTO® 60, SYTO® 61, SYTO® 62, SYTO® 63, SYTO® 64, SYTO® 80, SYTO® 81, SYTO® 82, SYTO® 83, SYTO® 84, SYTO® 85, thiazole orange (Aldrich Chemical Co., Milwaukee, Wis.), TO-PRO-1, TO-PRO-3, TO-PRO-5, TOTO-1, TOTO-2, TOTO™-3, YO-PRO®-1, YO-PRO®-3, YOYO-1, and YOYO®-3 (Molecular Probes, Inc., Eugene, Oreg.), among others.

SYBR® Green I (see, e.g., U.S. Pat. Nos. 5,436,134; 5,658,751; and/or 6,569,927), for example, has been used to monitor an amplification (e.g., PCR) reaction by amplifying the target sequence in the presence of the dye, exciting the biological sample with light at a wavelength absorbed by the dye and detecting the emission therefrom. It is to be understood that the use of the SYBR® Green dye is presented as an example and that many such dyes may be used in the methods described herein. Other nucleic acid binding agents can also be suitable as would be understood by one of skill in the art.

In certain embodiments, detection or measurement of the indicator of amplification in a digital amplification assay may be performed at the endpoint of the amplification reaction. The digital amplification may be detected or measured at an ambient temperature after one or more thermal cycles have been completed. It may be beneficial to detect indicators of amplification at other times (such as during amplification and/or during a melt stage) in order to better determine the amplicons produced.

Figure 1B:
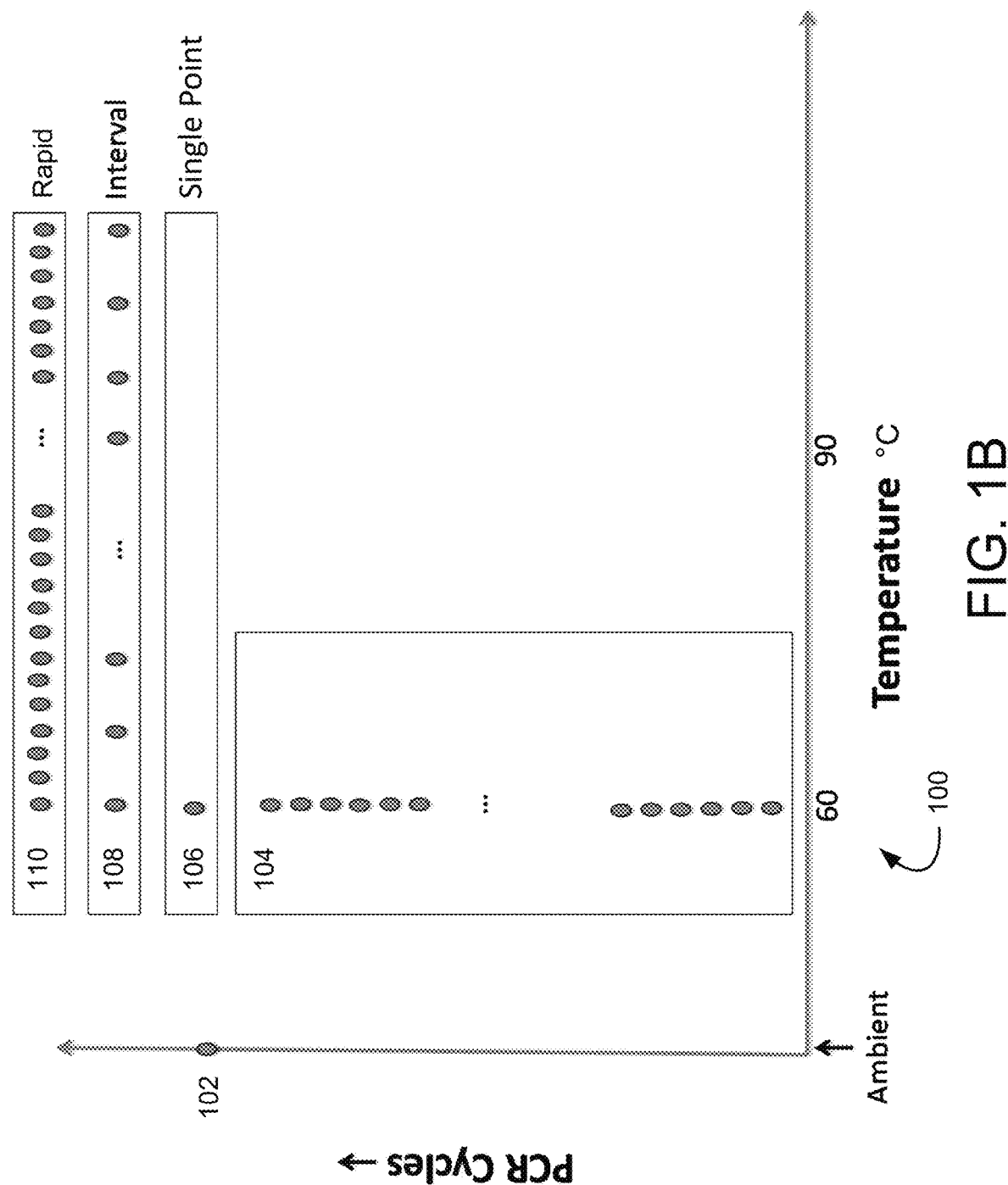
FIG. 1B illustrates exemplary techniques useful for detecting amplification of a target nucleic acid according to embodiments of the current invention.

FIG. 1B illustrates a graph illustrating various amplification detection schemes contemplated by the present disclosure, for example during an amplification assay or post-amplification (i.e., after completion of an amplification assay). For example, an indicator of amplification exhibited by reaction sites or reaction volumes hosting dPCR amplification may be subject to detection in each of these reaction sites or reaction volumes. As illustrated in FIG. 1B, detection point 102 corresponds to the endpoint detection at the ambient temperature described above.

In one exemplary embodiment, monitoring for an indicator of amplification occurring in the reaction sites may occur via a real-time detection scheme in which detection data is taken during the dPCR amplification assay. For example, the detection data may be obtained for each reaction site at a predetermined point during a thermal cycling process or procedure (e.g., at a predetermined temperature for one or more cycles of the thermal cycling process or procedure). Detection points 104 in FIG. 1B graphically represents the collection of such real time detection during amplification. As depicted, detection for an indicator of amplification under this real time technique relies on detection data taken during numerous PCR thermal cycles at the same temperature, e.g., at 60° C. In at least one exemplary embodiment, the real time detection occurs for each cycle of the total number of PCR cycles. In other exemplary embodiments, the real time detection occurs during a subset of cycles (e.g., predetermined subset, user selectable subset, or dynamic subset based on detected results), in accordance with a predetermined pattern of cycles based on the reagents used for amplification, or at any other suitable cycles.

In one exemplary embodiment, the present disclosure contemplates performing a melt stage on the reaction sites after the amplification assay and an end point reading has been performed. During such a melt stage, the sample reaction volumes in the reaction sites are heated at a constant rate over a predetermined time and changes to an indicator of amplification are detected. For example, the plurality of sample reaction volumes may be heated at a constant rate over a period of time, such as 10 minutes, 15 minutes, 30 minutes, 1 hour, or any other suitable period of time. During the heating, changes in an indicator of amplification for the sample reaction volumes may be detected, and changes in the indicators may be identified. For example, the bonds of a nucleic acid molecule may melt causing disassociation during heating. This disassociation may trigger a change (decrease) in the indicator of amplification exhibited.

Various exemplary post-amplification measurements are depicted as 106, 180 and 110 in FIG. 1B using various melt stage detection techniques. Detection point 106 comprises single point detection at a predetermined temperature, such as 60°, wherein the detection occurs during a melt stage post-amplification. For example, as a temperature for the sample in each of the reaction volumes is raised to 60°, the indicator of amplification exhibited by each reaction volume may be detected and changes determined. Detection points 108 correspond to interval detection at a plurality of predetermined target temperatures, for example starting at 60° and at certain higher temperatures as the heating increases. Detection points 110 correspond to a rapid detection technique over the predetermined time for the melt stage.

In exemplary embodiments, results for the detection point 102 may be combined with one or more of results for detection points 104, detection point 106, detection points 108, and/or detection points 110. The combined results may be analyzed to improve or enhance the accuracy of the dPCR detection or assay results. For example, the combined results may be used to correct for or eliminate contributions to an indicator signal that are produced by substances or molecules besides the target of interest (e.g., produced by a primer dimer). It will appreciate that not all of the various techniques 104, 106, 108, 110 need be performed for improving or enhancing the accuracy of a dPCR assay results, but rather one or more can be utilized and in various combinations to assist in improving or enhancing the accuracy of dPCR amplification detection or assay results.

FIGS. 2A, 2B, 3A, 3B, and 3C illustrate various exemplary methods that can be used to quantify dPCR amplification of a target nucleic acid based on data collected from one or more of the detection techniques illustrated in FIG. 1B.

Figure 2A:
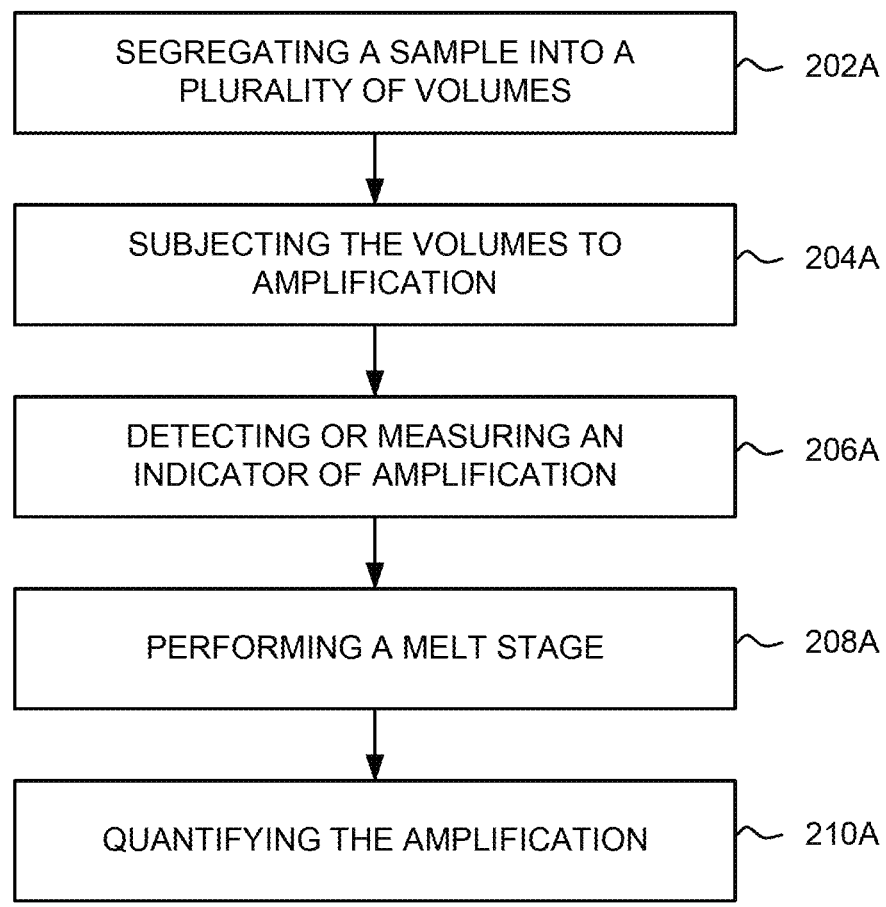
FIGS. 2A-2B illustrate exemplary methods of performing amplification that include a melt stage.
Figure 2B:
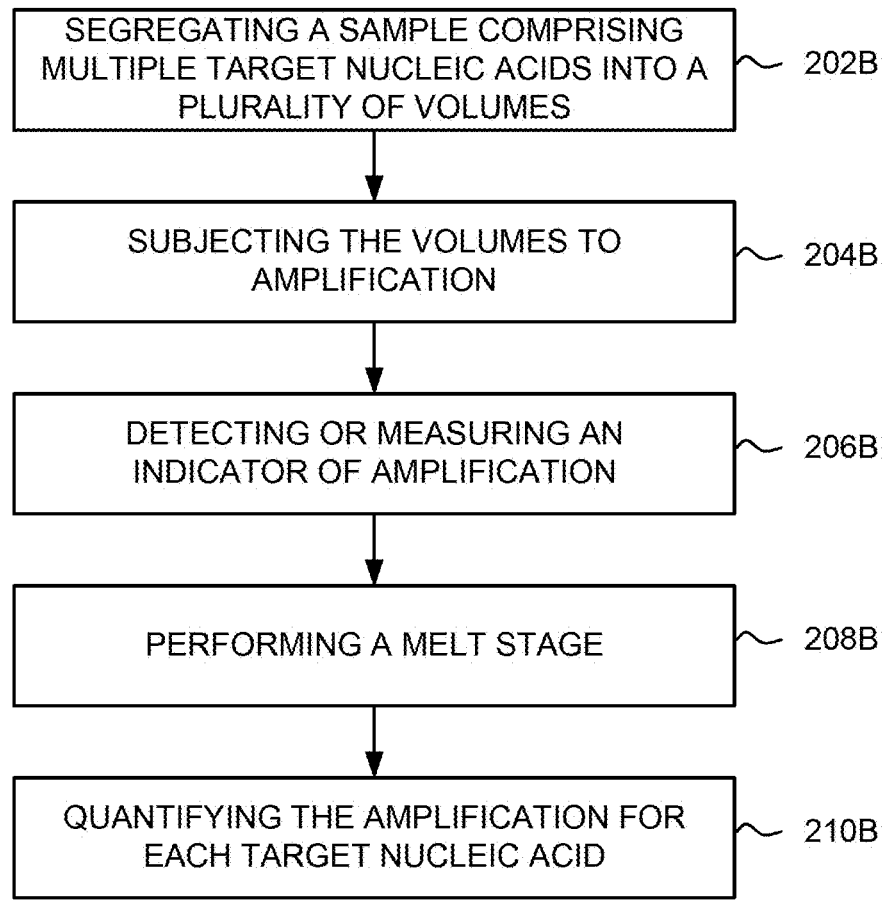

FIGS. 2A-2B illustrate exemplary methods for performing dPCR in accordance with embodiments of the present disclosure. The methods described herein may be performed with a variety of different reaction devices including, but not limited to a sample chip, an electronic chip, a circuit board, a TLDA card, droplets in a free solution, droplets on a planar surface, droplets over a temperature gradient, droplets in a capillary tube or flow system, a microfluidic device with individual chambers, a 384-well or higher density microtiter plate, an array of reaction wells, an array of through-holes in a substrate, or any other suitable reaction device. The method may comprise any of the detection techniques for dPCR with which those having ordinary skill in the art are familiar (e.g., optical detection or electrical detection). Various exemplary devices that may be utilized to implement the dPCR detection methods described herein are explained in further detail below.

At 202A of FIG. 2A, a sample is segregated, distributed, or divided into a plurality of sample reaction volumes. For example, the plurality of sample reaction volumes may be segregated such that a first plurality of the sample reaction volumes contain at least one molecule of a target nucleic acid and a second plurality of the sample reaction volumes contain no molecules of the target nucleic acid. The sample may be fractionated by a dilution process so that each sample reaction volume contains one copy, approximately one copy, or no copy of the target nucleic acid. In an embodiment, the segregated sample reaction volumes may include one or more reagents for amplifying the target nucleic acid molecules. The reagent(s) may be incorporated, mixed, or added into the sample prior to segregation or after segregation.

In one exemplary embodiment, the plurality of sample reaction volumes may be segregated on a sample holder 900 of FIG. 9, or the like, described in further detail below, although various other reaction devices may be used to segregate the sample reaction volumes and implement the amplification detection techniques described herein and/or known in the art. Accordingly, the sample reaction volumes may be segregated among the plurality of reaction sites (e.g., through-holes or wells) of sample holder 900.

At 204A, the plurality of sample reaction volumes are subjected to an amplification assay. For example, the plurality of sample reaction volumes may be simultaneously subjected to an amplification assay, wherein the amplification assay is designed to amplify the target nucleic acid to produce amplified product (i.e., one or more amplicons). The assay may utilize at least a primer, probe and/or dye, and an enzyme, such as a Taqman™ assay or any other suitable assay, as those having ordinary skill in the art are familiar with. Accordingly, the sample reaction volumes contain the sample portion and the reagents for amplification and detection.

In some embodiments, an assay may include two probes, such as a FAM™ dye-labeled probe and a VIC® dye-labeled probe, and amplification detection measurements based on each dye may be utilized in order to determine quantities for amplified target nucleic acid(s). For instance, multiple indicators of amplification may be exhibited from a sample reaction volume based on each of the dye-labeled probes. An assay may also include a variety of primers, such as ELITe® primers. In an embodiment, one ELITe® primer may overlap a target sequence (i.e., an allele specific primer) while one ELITe® primer may not (i.e., a locus specific primer). Some implementations may leverage a standard primer rather than an ELITe® primer for the locus specific primer. In some embodiments, a multiplexing assay may be used where multiple allele specific primers may generate amplicons with a single locus specific primer.

In some embodiments, an assay may include primers with target specific 3' domains and non-target specific 5' tails to generate amplicons with adjusted target melt temperatures. In another example, an assay may include primers with target specific 3' domains and universal 5' tails to generate amplicons with adjusted target melt temperatures. In this example, the assay formulations may utilize universal primers such that initial amplification is caused by target specific domains (e.g., target specific 3' domain) while further amplification can be caused by the universal primers. These amplicons may be later differentiated by target melt temperatures. In some embodiments, an assay may include primers designed to identify amplification reactions involving normal (wild-type) nucleic acids and non-normal (mutant) nucleic acids. An assay may also include primers designed to identify certain types of mutations (i.e., single nucleotide polymorphisms (SNPs) and inDels at locus within amplicons). For instance, the identification may be based on target melt temperatures for the produced amplicons. In some embodiments, use of known spike-in concentrations may also be leveraged for identification. Various embodiments may utilize ELITe® primers, non-ELITe® (standard) primers, or any suitable combination.

In an exemplary embodiment, the plurality of sample reaction volumes subjected to the amplification assay may be subjected to a plurality of PCR steps, such as thermal cycling, as described herein. For example, a temperature of the sample reaction volumes may be increased to physically separate strands of the target nucleic acid (i.e. strands of a nucleic acid molecule). The temperature may then be decreased and each strand may be used as a template for synthesis by an enzyme (i.e., polymerase) to selectively amplify the target nucleic acid, for instance during annealing and extension phases of the PCR process. In an embodiment, a plurality of PCR cycles may be performed that result in amplification of the target nucleic acid molecule.

At 206A, an indicator of amplification presented by the plurality of sample reaction volumes may be detected or measured. For example, an indicator of amplification may be presented by each of the plurality of sample reaction volumes that host amplification of a nucleic acid molecule (e.g., amplification of the target nucleic acid molecule).

In an embodiment, one or more dyes may be used that fluoresce when bound to double-stranded nucleic acids, and this fluorescence may be detected as an indicator of amplification. For example, the nucleic acid binding agent (dye) may produce a detectable signal when bound to double-stranded nucleic acids that is distinguishable from the signal produced when that same agent is in solution or bound to a single-stranded nucleic acid. The fluorescence may be detected using a fluorescence detector, for example mounted over a chip that houses the segregated sample reaction volumes, or may be detected in any other suitable manner.

Figure 4:
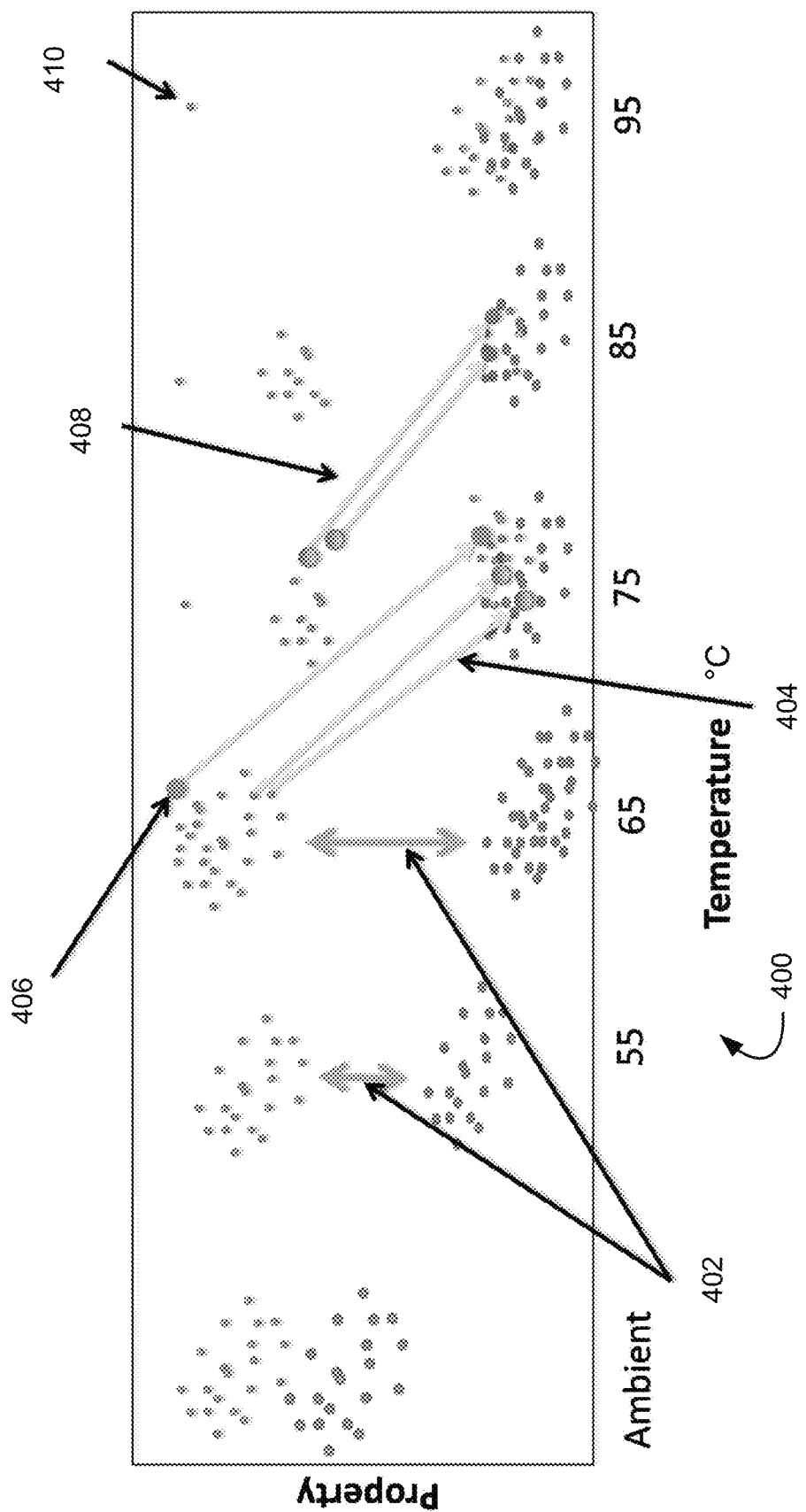
FIG. 4 illustrates a graph of illustrative, prophetic exemplary amplification detection data taken at interval temperatures.

In an exemplary embodiment, an indicator of amplification may be detected for each of the plurality of reaction volumes at a first temperature. For example, an initial detection for an indicator of amplification may occur while the volumes are at a first temperature, which according to various exemplary embodiments may be ambient temperature. FIG. 4 illustrates a graph of exemplary, prophetic detection results. An indicator of amplification (e.g., fluorescence) for the sample reaction volumes may be represented by the "Property" attribute on the y-axis and the temperature may be represented by the x-axis. Accordingly, the indicator of amplification presented by the reaction volumes detected at an ambient temperature are illustrated in the graph of FIG. 4.

At 208A, a melt stage is performed, for example, after discontinuing the amplification assay during 204A. During the melt stage, the plurality of sample reaction volumes may be heated at a constant rate over a predetermined time and changes to an indicator for the sample reaction volumes are identified based on the heating. For example, the plurality of sample reaction volumes may be heated at a constant rate over a period of time, such as 10 minutes, 15 minutes, 30 minutes, 1 hour, or any other suitable period of time. During the heating, the results for the indicator of amplifications (e.g., fluorescence) for the sample reaction volumes may be detected, and changes in the indicator may be identified. For example, the bonds of a nucleic acid molecule may melt causing disassociation during heating of the sample reaction volumes. This disassociation triggers a change (e.g., a decrease) in the indicator of amplification exhibited by a sample reaction volume. For example, one or more dyes that fluoresce to produce the indicator of amplification while bound to double-stranded nucleic acid molecules may cease to produce such an indicator (or produce less of the indicator) when the molecules undergo disassociation.

In an embodiment, the indicator of amplification (e.g., fluorescence) for the sample reaction volumes may be detected at a series of intervals during the melt. As discussed above, detection points 108 of FIG. 1B illustrate this type of interval detection scheme, and FIG. 4 further illustrates a graph 400 of illustrative, prophetic exemplary detection results, where the indicator may be detected at various target temperatures. In an embodiment, the target temperatures may be based on temperature intervals (e.g., 5° C., 10° C., and the like), or may be a predetermined set of target temperatures. In FIG. 4, the target temperatures include 55° C., 65° C., 75° C., 85° C., and 95° C. At each target temperature, detection of the reactions in each of the plurality of reaction volumes can occur such that changes in the indicator of amplification may be identified. For example, the results for detection at ambient temperature (e.g., initial detection) may be compared to the results detected at 55° C. The comparison shows that a set of sample reaction volumes from the plurality of reaction volumes exhibits a decrease in the indicator of amplification between ambient temperature and 55° C., e.g., as melting begins. Similarly, comparisons between results detected for target temperatures 55° C. and 65° C., 65° C. and 75° C., 75° C. and 85° C., and 85° C. and 95° C. show decreases in the indicators of amplification for the sample reaction volumes.

In an embodiment, the results for the indicator of amplification (e.g., fluorescence) for the sample reaction volumes may be detected rapidly during the melt. For example, detection may occur at closely spaced intervals such that a continuous data function may be generated. As discussed above, detection points 110 of FIG. 1B illustrate this type of rapid detection scheme. In analyzing the results detected rapidly, trends for the indicators exhibited by the plurality of reaction volumes may be determined. For example, the analysis may show a trend that a set of sample reaction volumes from the plurality of reaction volumes exhibits a decrease in the indicator of amplification as the melt progresses (e.g., temperature of the reaction volumes increases). The trends may be similar to results determined from comparisons during interval detection during a melt. In an example, trends between temperatures similar to the target temperatures of an interval detection method, such as ambient and 55° C., 55° C. and 65° C., 65° C. and 75° C., 75° C. and 85° C., and 85° C. and 95° C., may be determined based on the analysis.

In an exemplary embodiment, the rapid detection also may enable identification of trends at specific temperatures (e.g., temperatures other than the target temperatures of the interval detection). For example, during the melt, a temperature (or temperature window) may trigger a noticeable change (e.g., change beyond a threshold) for the indicators exhibited by the reaction volumes. The rapid detection may enable identification of these temperatures, or temperature window, via analysis of the changes in the indicators. Accordingly, the rapid detection methodology may provide enhanced sensitivity to the analysis.

At 210A, the amplification of the target nucleic acid may be quantified based on the initial detected indicators and the detected changes in the indicators. For example, the indicators exhibited by the reaction volumes at ambient temperature may suggest a level of amplification that occurred in each reaction volume over the PCR process. However not all of the detected amplified product is a result of amplification of the target nucleic acid. In other words, the indicators presented by the reaction volumes at ambient temperature may indicate amplification of something other than the target nucleic acid, or may be triggered by some other source, yet erroneously detected as the amplified product of the target nucleic acid. Such erroneously detected amplified product can include, for instance, primer-dimers, misincorporations, dust/debris, sample nucleic acid, or various other sources. As used herein, the term "erroneous amplification product" means an amplification product produced by nucleic acid molecules that are not a target nucleic acid. Performance of the melt and a subsequent analysis of the detected results may enable identification of indicators that are not the results of the desired amplification of the target nucleic acid. After considering the indicators that are related to some other source, the amplification for the target nucleic acid may be quantified with greater accuracy.

In an embodiment, a single point detection algorithm may be used with the endpoint detection (e.g., at ambient temperature), as illustrated by detection point 106 of FIG. 1B described above. For example, an identified change may be determined based on the detection results at ambient temperature (e.g., detection point 102) and the predetermined temperature for single point detection (e.g., detection point 106). One of identified changes 402 in FIG. 4 may include the identified change based on the single point detection.

For example, the detected change at this temperature may include a further separation of the reaction volumes that exhibit indicators of amplification triggered by nucleic acid amplification from the reaction volumes that do not. Reaction volumes that exhibit some indicator of amplification may show a decrease such that the background noise of the results is reduced. For example, when a dye, such a SYBR dye (or other intercalating dye), is used to produce the indicator of amplification, the dye may bond with various reaction products (e.g., nucleic acids) due to the non-specific design of the dye. Accordingly, background noise (e.g., fluorescence) may be caused by dye binding to anilities which are not products of the reaction, or binding to products which are not the intended product of the reaction. In an embodiment, reaction volumes that exhibit the indicator of amplification may be discernible from those that do not based on the further separation, and the amplification of the target nucleic acid may be more accurately quantified based on the discerned reaction volumes.

In an embodiment, an interval detection algorithm may be used with the endpoint detection (e.g., at ambient temperature), as illustrated by detection points 108 of FIG. 1B. For example, identified changes may be determined based on the detection results at ambient temperature (e.g., detection point 102) and the predetermined temperatures for interval detection (e.g., detection points 108).

In one embodiment, the identified changes in the indicators for the plurality of reaction volumes may be analyzed to determine indicators triggered by a source other than amplification of the target nucleic acid. For example, based on the particular target nucleic acid, an expected melt temperature (or expected melt temperature range) may be determined such that the target nucleic acid would be expected to melt at the temperature. Therefore, an indicator exhibited by a reaction volume based on amplification of the target nucleic acid would be expected to decrease at the expected melt temperature or temperature range (e.g., fluorescence exhibited by a reaction volume would be expected to decrease at the expected melt temperature). The expected melt temperature may be specific to a target nucleic acid, the amplification assay used during amplification, particular primers, and any other suitable factor for amplification. In an example, the expected melt temperature for a target nucleic acid (being amplified using a specific amplification assay) may be determined using empirical analysis (e.g., amplified target nucleic acid molecules may be heated until disassociation, and the temperature when disassociation occurs may be the melt temperature).

In an embodiment, during performance of the melt, indicator detection may occur at various temperature intervals. FIG. 4 illustrates a graph of illustrative, prophetic exemplary detection results based on interval temperatures. In an example, the expected melt temperature for the target nucleic acid here may comprise 70° C., or an expected melt temperature range may comprise 65° C. to 75° C.

Identified change 404, detected at temperature 75° C., may indicate changes to indicators triggered by amplification of the target nucleic acid. Because the expected melt temperature for the target nucleic acid comprises 70° C., or a range between 65° C. to 75° C., the decreases of indicators detected at 75° C. correspond to indicators triggered by amplification of the target nucleic acid. For instance, indicator 406 illustrates one or more indicators exhibited by reaction volumes where the indicators decrease (e.g., a decrease in fluorescence) during the detection at 75° C. Accordingly, quantifying the decrease in indicators exhibited by the plurality of reaction volumes between 65° C. and 75° C. (e.g., identified change 404) may enable the quantification of amplicon (amount of amplified target nucleic acid) that resulted from the dPCR amplification.

Identified change 408, detected at temperature 85° C., may indicate changes to indicators triggered by a source other than amplification of the target nucleic acid. Because the expected melt temperature for the target nucleic acid comprises 70° C., or a range between 65° C. to 75° C., the decreases of indicators detected at 85° C. correspond to indicators triggered by other sources. Indicator 410, detected at temperature 95° C., also corresponds to indicators triggered by a source other than amplification of the target nucleic acid sequence. At such a high temperature, nucleic acids would be expected to melt, and therefore indicator 410 may correspond to a source like dust, or some other source that may cause an indicator to persist above certain temperature thresholds.

In an embodiment, during performance of the melt, indicator detection also may occur rapidly in lieu of or in addition to set temperature point interval detection. For example, the rapid detection scheme may be used with the endpoint detection (e.g., at ambient temperature), as illustrated by detection points 110 of FIG. 1B. In this way, identified changes may be determined based on the detection results at ambient temperature (e.g., detection point 102) and rapidly over the melt temperature range (e.g., detection points 110).

Similar to the interval detection analysis, the identified changes to indicators for the plurality of reaction volumes at various temperatures may be compared to an expected melt temperature for the target nucleic acid. For example, indicators that show changes (e.g., decreases) at temperatures other than the expected melt temperature (or expected melt temperature range) for the target nucleic acid may correspond to sources other than target nucleic acid amplification (e.g., the indicators may be triggered by something other than target nucleic acid amplification). On the other hand, indicators that show changes (e.g., decreases) at the expected melt temperature (or expected melt temperature range) for the target nucleic acid may correspond to target nucleic acid amplification (e.g., the indicators may be triggered by target nucleic acid amplification).

In an embodiment, based on the detected changes in the indicators during the melt stage, the amount of amplified product of the target nucleic acid resulting from the amplification process may be quantified. For example, the amount of amplified product may be directly proportional to the change detected for indicators (e.g., detected decrease in fluorescence) at the expected melt temperature (or expected melt temperature range). In an embodiment, the quantification may be based on identification of indicators triggered by a source other than target nucleic acid amplification. For example, it may be determined that indicators that changed (e.g., decreased) at temperatures other than the expected melt temperature (or expected melt temperature range) correspond to sources other than target nucleic acid amplification. Accordingly, these indicators may be discounted when quantifying the amplification of the target nucleic acid.

In an embodiment, detected changes for indicators at an expected melt temperature (or an expected melt temperature range) may confirm expected amplification, and amplification of the target nucleic acid may be quantified based on these confirmed indicators. For example, a Poisson model may be used along with a total number of sample reaction volumes and total number of non-amplifying sample reaction volumes, distinguished using indicator changes at an expected melt temperature, to calculate a mean number of reactions per sample reaction volume. The result can be divided by the mean volume of each sample reaction volume to arrive at the copies per unit volume for the reaction product melting at the expected melt temperature or temperature range.

FIG. 2B illustrates an exemplary method for performing digital amplification (dPCR) using multiplexing in accordance with at least one exemplary embodiment of the present disclosure. The method described herein may be performed with the sample chip, a circuit board comprising through holes, or with any other suitable device and detection scheme for dPCR with which those having ordinary skill in the art are familiar.

At 202B of FIG. 2B, a sample is segregated, distributed, or divided into a plurality of sample reaction volumes. In one exemplary embodiment, the sample may comprise two or more different target nucleic acids. For example, the dPCR process of the method may comprise a multiplexed amplification such that more than one target nucleic acid is amplified. The plurality of sample reaction volumes may be segregated such that a first plurality of the sample reaction volumes contain at least one molecule of one of the target nucleic acids and a second plurality of the sample reaction volumes contain no molecules of the target nucleic acids. The sample may be fractionated by a dilution process so that each sample reaction volume contains one copy, approximately one copy, or no copy of the nucleic acid template or target. In an embodiment, the segregated sample reaction volumes may include a plurality of reagents for amplifying one or more target nucleic acid molecules. The reagents may be incorporated into the sample prior to segregation or after segregation.

In one exemplary embodiment, the plurality of sample reaction volumes may be segregated on a sample holder similar to sample holder 900 of FIG. 9, described in further detail below. Accordingly, the sample reaction volumes may be segregated among the plurality of reaction sites (e.g., a plurality of wells or through-holes) of chip 900. In an embodiment, a circuit board may comprise a plurality of through-holes, and the plurality of sample reaction volumes may be segregated among the plurality of through-holes.

Referring again to FIG. 2B, at 204B, the plurality of sample reaction volumes are subjected to an amplification assay. For example, the plurality of sample reaction volumes may be simultaneously subjected to a multiplexing amplification assay, wherein the multiplexing amplification assay is designed to amplify multiple target nucleic acids to produce amplified product (i.e., one or more amplicons). The multiplexing assay may comprise at least a probe, a primer, and an enzyme, such as a Taqman™ assay or any other suitable assay. In one exemplary embodiment, the multiplexing assay includes reagents (e.g., primers and/or probes) specific to each of the multiple types of target nucleic acids such that each target nucleic acid sequence, if present in a reaction site, may be amplified by exposure to the assay. Reagents (e.g., primers and/or probes) of the multiplexing assay may be designed such that each target nucleic acid is amplified, and the resultant amplicons may later be differentiated based on target melt temperatures. In some instances, expected target melt temperatures for amplicons may be based on the designed primers pairs used to amplify the target nucleic acids. The multiplexing assay may be designed for two, three, four, or more target nucleic acids, and the resultant amplicons may be differentiated based on the results of a melt, as described herein.

In some embodiments, a multiplexing assay may include two probes, such as a FAM™ dye-labeled probe and a VIC® dye-labeled probe, and amplification detection results based on each dye may be utilized in order to determine quantities for amplified target nucleic acid(s). For instance, multiple indicators of amplification may be exhibited from a sample reaction volume based on each of the dye-labeled probes. A multiplexing assay may also include a variety of primers, such as ELITe® primers. In an embodiment, one ELITe® primer may overlap a target sequence (i.e., an allele specific primer) while one ELITe® primer may not (i.e., a locus specific primer). Some implementations may leverage a standard primer rather than an ELITe® primer for the locus specific primer. In some embodiments, a multiplexing assay may be used where multiple allele specific primers may generate amplicons with a single locus specific primer.

In some embodiments, a multiplexing assay may include primers with target specific 3' domains and non-target specific 5' tails to generate amplicons with adjusted target melt temperatures. In another example, a multiplexing assay may include primers with target specific 3' domains and universal 5' tails to generate amplicons with adjusted target melt temperatures. In this example, the assay formulations may utilize universal primers such that initial amplification is caused by target specific domains (e.g., target specific 3' domain) while further amplification can be caused by the universal primers. These amplicons may be later differentiated by target melt temperatures. In some embodiments, a multiplexing assay may include primers designed to identify amplification reactions involving normal (wild-type) nucleic acids and non-normal (mutant) nucleic acids. An assay may also include primers designed to identify certain types of mutations (i.e., SNPs and inDels at locus within amplicons). For instance, the identification may be based on target melt temperatures for the produced amplicons. In some embodiments, use of known spike-in concentrations may also be leveraged for identification. Various embodiments may utilize ELITe® primers, non-ELITe® (standard) primers, or any suitable combination. In an embodiment, the plurality of sample reaction volumes subjected to the multiplexing amplification assay may be further subjected to a plurality of amplification steps, such as thermal cycling, as described herein. For example, a temperature of the sample reaction volumes may be increased to physically separate strands of the target nucleic acid (i.e. strands of a nucleic acid molecule). The temperature may then be decreased and each strand may be used as a template for synthesis by an enzyme (i.e., polymerase) to selectively amplify the target nucleic acids, for instance during annealing and extension phases of the amplification process. In an embodiment, a plurality of amplification cycles may be performed that result in amplification of the target nucleic acid molecules.

At 206B, an indicator of amplification presented by the plurality of sample reaction volumes may be detected or measured. For example, an indicator of amplification may be presented by each of the plurality of sample reaction volumes that host amplification of a nucleic acid molecule (e.g., amplification of one of the target nucleic acid molecules).

In an embodiment, one or more dyes may be used that fluoresce when bound to double-stranded nucleic acids, and this fluorescence may be detected as an indicator of amplification. For example, the nucleic acid binding agent (dye) may produce a detectable signal when bound to double-stranded nucleic acids that is distinguishable from the signal produced when that same agent is in solution or bound to a single-stranded nucleic acid. The fluorescence may be detected using a fluorescence detector, for example mounted over a chip that houses the segregated sample reaction volumes, or may be detected in any other suitable manner. In an exemplary embodiment, indicator(s) of amplification presented by the plurality of reaction volumes may be detected at a first temperature. For example, an initial detection may comprise the indicators for amplification of a plurality of sample reaction volumes while the volumes are at a first temperature, which according to various exemplary embodiments may be ambient temperature. Detection point 102 of FIG. 1B may illustrate detection of the indicator presented by the plurality of reaction site at an ambient temperature.

At 208B, a melt stage is performed, for example, after discontinuing the amplification assay during 204A. During the melt stage, the plurality of sample reaction volumes are heated at a constant rate over a predetermined time and changes in the indicators for the plurality of sample reaction volumes are identified based on the heating. For example, the plurality of sample reaction volumes may be heated at a constant rate over a period of time, such as 10 minutes, 15 minutes, 30 minutes, 1 hour, or any other suitable period of time. During the heating, the results for the indicators of amplifications (e.g., fluorescence) for the plurality of sample reaction volumes may be detected, and changes in the indicators may be identified.

In an embodiment, the indicators of amplifications (e.g., fluorescence) for the plurality of sample reaction volumes may be detected at a series of intervals during the melt. Detection points 108 of FIG. 1B illustrate this type of interval detection algorithm. In an embodiment, the indicators may be detected at various target temperatures based on temperature intervals (e.g., 5° C., 10° C., and the like), or a predetermined set of target temperatures. At each target temperature, detection of the reactions in each of the plurality of reaction volumes can occur such that changes in the indicators of amplification may be identified. For example, the results may be similar to the detection results illustrated in FIG. 4 for singleplex digital amplification.

In an embodiment, the results for the indicators of amplifications (e.g., fluorescence) for the plurality of sample reaction volumes may be detected rapidly during the melt such that a continuous function may be generated. Detection points 110 of FIG. 1B illustrate this type of rapid detection algorithm. In analyzing the results detected rapidly, trends for the indicators exhibited by the plurality of reaction volumes may be determined. For example, the analysis may show a trend that a set of sample reaction volumes from the plurality of reaction volumes exhibits a decrease in the indicator of amplification as the melt progresses (e.g., temperature of the reaction volumes increases). The trends may be similar to results determined from comparisons during interval detection during a melt.

At 210A, the amplification of the target nucleic acid may be quantified based on the initial detected indicators and the detected changes in the indicators. For example, the indicators exhibited by the reaction volumes at ambient temperature may suggest a level of amplification that occurred in each reaction volume over the amplification process, however not all of the detected amplified product is a result of amplification of one of the target nucleic acids. In other words, the indicators presented by the reaction volumes at ambient temperature may indicate amplification of something other than one of the target nucleic acids, or may be triggered by some other source, yet erroneously detected as the amplified product. Such erroneously detected amplified product can include, for instance, primer-dimers, misincorporations, dust/debris, or various other sources.

Moreover, in one exemplary embodiment, indicators of amplification exhibited by the reaction site triggered by amplification of one of the target nucleic acids are not discernible based on the particular target nucleic acid amplified. In other words, in a multiplexing digital amplification process, indicators of amplification triggered by an expected amplicon are not specific to one of the target nucleic acids, and therefore it cannot be determined which target nucleic acid triggered the indicator of amplification. Performance of the melt and a subsequent analysis of the detected results may enable identification of indicators that are not the results of amplification of the target nucleic acid and identification of indicators specific to each of the multiple target nucleic acids. After considering the indicators that are related to some other source, the amplification for each target nucleic acid may be quantified with greater accuracy.

In an embodiment, an interval detection algorithm may be used with the endpoint detection (e.g., at ambient temperature), as illustrated by detection points 108 of FIG. 1B. For example, identified changes may be determined based on the detection results at ambient temperature (e.g., detection point 102) and the predetermined temperatures for interval detection (e.g., detection points 108).

In one embodiment, the identified changes in the indicators for the plurality of reaction volumes may be analyzed to determine indicators triggered by a source other than amplification of the target nucleic acid. For example, based on the particular target nucleic acids, expected melt temperatures (or expected melt temperature ranges) may be determined such that the amplified target nucleic acids would be expected to melt at the temperatures. Therefore, an indicator exhibited by a reaction volume based on amplification of the target nucleic acid would be expected to decrease at one of the expected melt temperatures or temperature ranges (e.g., fluorescence exhibited by a reaction volume would be expected to decrease at one of expected melt temperatures).

In an example, the expected melt temperatures for a first type of target nucleic acid may be 60° C., or an expected melt temperature range be from 55° C. to 65° C., and an expected melt temperature for a second type of target nucleic acid may be 70° C., or an expected melt temperature range may be from 65° C. to 75° C. Therefore, an identified change to an indicator of amplification at 60° C., or between 55° C. to 65° C., may indicate changes to indicators triggered by amplification of the first type of target nucleic acid. Similarly, an identified change to an indicator of amplification at 70° C., or between 65° C. to 75° C., may indicate changes to indicators triggered by amplification of the second type of target nucleic acid. Identified changes to indicators at other temperatures, or temperature ranges, may indicate changes to indicators triggered by a source other than amplification of a target nucleic acid.

In an embodiment, during performance of the melt, indicator detection also may occur rapidly in lieu of or in addition to set temperature point interval detection. For example, rapid detection algorithm may be used with the endpoint detection (e.g., at ambient temperature), as illustrated by detection points 110 of FIG. 1B. For example, identified changes may be determined based on the detection results at ambient temperature (e.g., detection point 102) and rapidly over the melt temperatures (e.g., detection points 110).

Similar to the interval detection analysis, the identified changes to indicators for the plurality of reaction volumes at various temperatures may be compared to expected melt temperatures for the multiple target nucleic acids. For example, indicators that show changes (e.g., decreases) at temperatures other than the expected melt temperatures (or expected melt temperature ranges) for the target nucleic acids may correspond to sources other than target nucleic acid amplification (e.g., the indicators may be triggered by something other than target nucleic acid amplification). On the other hand, indicators that show changes (e.g., decreases) at the expected melt temperatures (or expected melt temperature ranges) for the target nucleic acids may correspond to target nucleic acid amplification (e.g., the indicators may be triggered by target nucleic acid amplification).

In an embodiment, based on the detected changes in the indicators during the melt, the amplified product of the target nucleic acid resulting from the amplification process may be quantified. For example, the amplified product of the first type of target nucleic acid may be directly proportional to the change detected for indicators (e.g., detected decrease in fluorescence) at the expected melt temperature (or expected melt temperature range) for the first type of target nucleic acid and the amplified product of the second type of target nucleic acid may be directly proportional to the change detected for indicators (e.g., detected decrease in fluorescence) at the expected melt temperature (or expected melt temperature range) for the second type of target nucleic acid. In an embodiment, the quantification may be based on identification of indicators triggered by a source other than target nucleic acid amplification. For example, it may be determined that indicators that changed (e.g., decreased) at temperatures other than the expected melt temperatures (or expected melt temperature ranges) correspond to sources other than target nucleic acid amplification. Accordingly, these indicators may be discounted when quantifying the amplification of the target nucleic acids.

In an embodiment, clustering of measured melt temperatures may be used to identify target nucleic acid amplification and quantify amplified target nucleic acids. For example, decreases to a plurality of indicators of amplification associated with a plurality of sample reaction volumes may be measured at a particular temperature (or within a temperature range) to determine melt temperatures for these indicators, as described herein. These measured melt temperatures may be clustered, for example, based on calculated Euclidean distances and/or calculated silhouette values such that clusters of indicators with similar melt temperatures may be determined. Reference is made to *HRM Experiments, Using MeltDoctor™ HRM Reagents and High Resolution Melt Software* v3.0, Life Technologies, 2010, which reviews the use of silhouette scores for clustering when performing a melt using available software tools. Those of ordinary skill in the art will recognize various additional techniques exist for clustering data that may be implemented to obtain clusters for the purposes of the present embodiments. Accordingly, one or more clusters may be identified that comprise indicators of amplification with similar melt temperatures.

In some embodiments, an indicator of amplification may be confirmed as indicating target nucleic acid amplification when the indicator is determined to be within an identified cluster of melt temperatures. For example, a first identified cluster may be associated with a first target nucleic acid based on a comparison between the measured melt temperature (or melt temperature range) for the identified cluster and the expected melt temperature for the first target nucleic acid. Similarly, a second identified cluster may be associated with a second target nucleic acid based on a comparison between the measured melt temperature (or melt temperature range) for the identified cluster and the expected melt temperature for the second target nucleic acid. In such an embodiment, indicators may be confirmed for each target nucleic acid based on the identified melt temperature cluster for the indicators. In some embodiments, it may be determined that indicators that are not within one of the identified clusters do not comprise amplified target nucleic acid. Accordingly, these indicators may be discounted when quantifying the amplification of the target nucleic acids.

In an embodiment, amplification of each target nucleic acid may be quantified based on indicators of amplification confirmed by clustering for each target nucleic acid, as described herein, or indicators of amplification confirmed based on an expected melt temperature (or an expected melt temperature range) for each target nucleic acid. For example, a Poisson model may be used along with a total number of sample reaction volumes and total number of non-amplifying sample reaction volumes, distinguished using indicators changes at an expected melt temperature or indicators that are not part of a cluster, to calculate a mean number of reactions per sample reaction volume. The result can be divided by the mean volume of each sample reaction volume to arrive at the copies per unit volume for the reaction product melting at the expected melt temperature or temperature range.

FIGS. 3A-3D illustrate another exemplary method for performing dPCR. The method described herein may be performed with the sample chip, as described further below, a circuit board comprising through holes, or with any other suitable device, such as the exemplary devices described herein. For example, FIGS. 3A-3D may describe methods for performing dPCR and quantifying a target nucleic acid using an end point detection scheme together with one or more of real-time detection, single point detection, interval detection, and rapid detection, as illustrated in FIG. 1B.

Figure 3A:
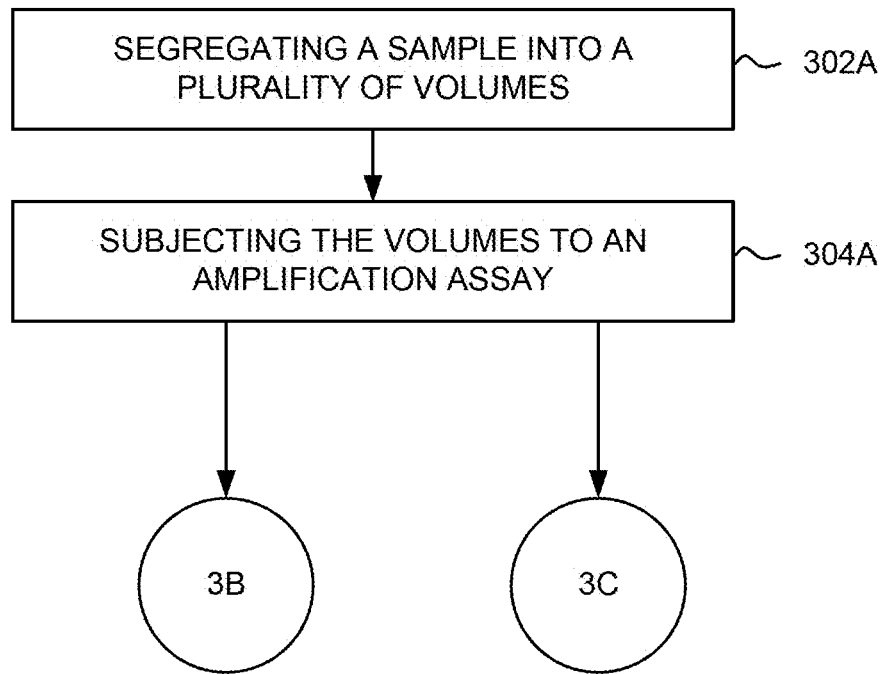
FIGS. 3A-3D illustrate exemplary methods of performing amplification with detection techniques.

At 302A of FIG. 3A, a sample may be segregated, distributed, or divided into a plurality of sample reaction volumes. For example, the plurality of sample reaction volumes may be segregated such that a first plurality of the sample reaction volumes contain at least one molecule of a target nucleic acid and a second plurality of the sample reaction volumes contain no molecules of the target nucleic acid. The sample may be fractionated by a dilution process so that each sample reaction volume contains one copy, approximately one copy, or no copy of the nucleic acid template or target, copy of the target nucleic acid or less. In an embodiment, the sample reaction volumes may range from about 1 aL to 50 uL. In other embodiments, the reaction volumes may be approximately 1 nL, 1 pL, 33 nL, or any other suitable volume.

In one exemplary embodiment, the plurality of sample reaction volumes may be segregated on a sample holder similar to sample holder 900 of FIG. 9, described in further detail below, although various other devices may be used to segregate the sample reaction volumes and implement the amplification detection techniques described herein. Accordingly, the sample reaction volumes may be segregated among the plurality of reaction sites (e.g., wells or through-holes) of sample holder 900.

At 304A, the plurality of sample reaction volumes are subjected to an amplification assay. For example, the plurality of sample reaction volumes may be simultaneously subjected to an amplification assay, wherein the amplification assay is designed to amplify a target nucleic acid to produce amplified product (i.e., amplicons). The assay may comprise at least a probe, a primer, and an enzyme, such as a Taqman™ assay or any other suitable assay.

Figure 3B:
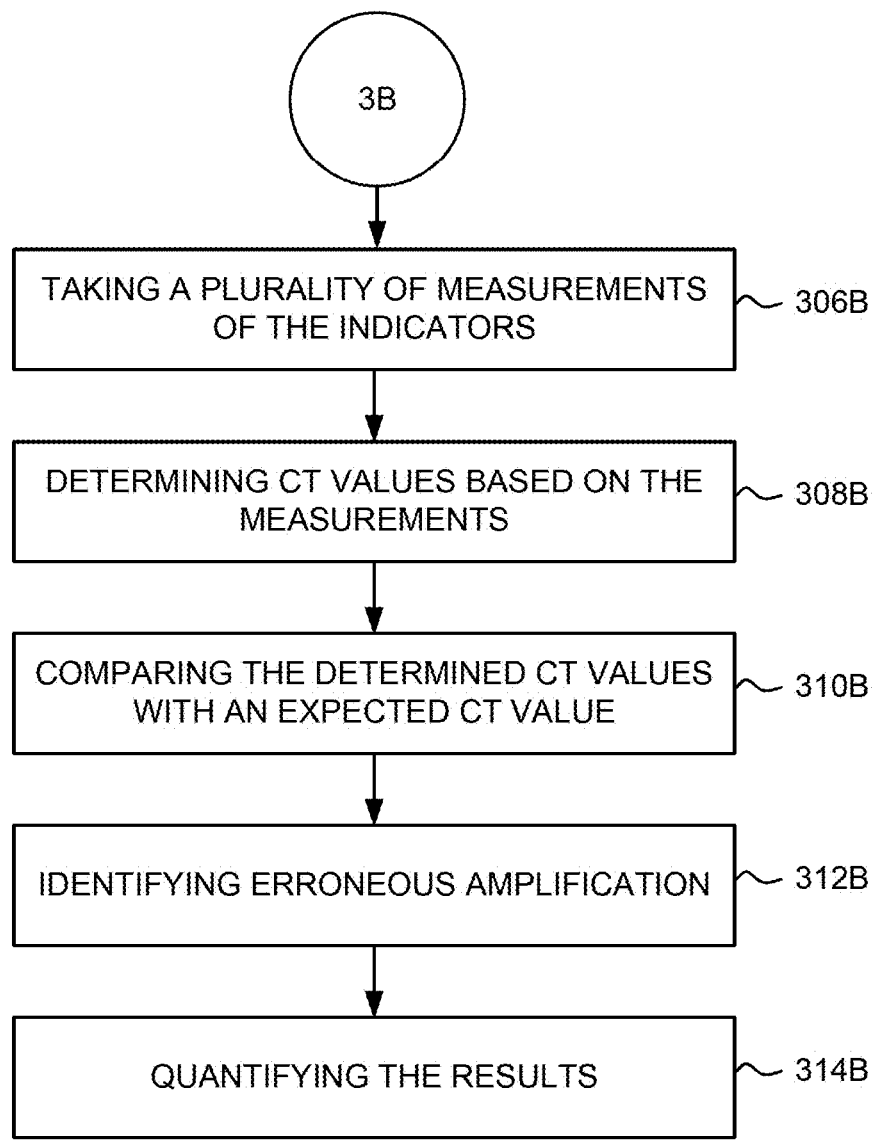

In one embodiment, the method of FIG. 3A may progress to 306B of FIG. 3B, where real time detection may be used to quantify target nucleic acid amplification. For example, detection points 104 of FIG. 1B may illustrate real time detection during digital amplification, and this real time detection may be used to quantify the amplification of the target nucleic acid.

Figure 3C:
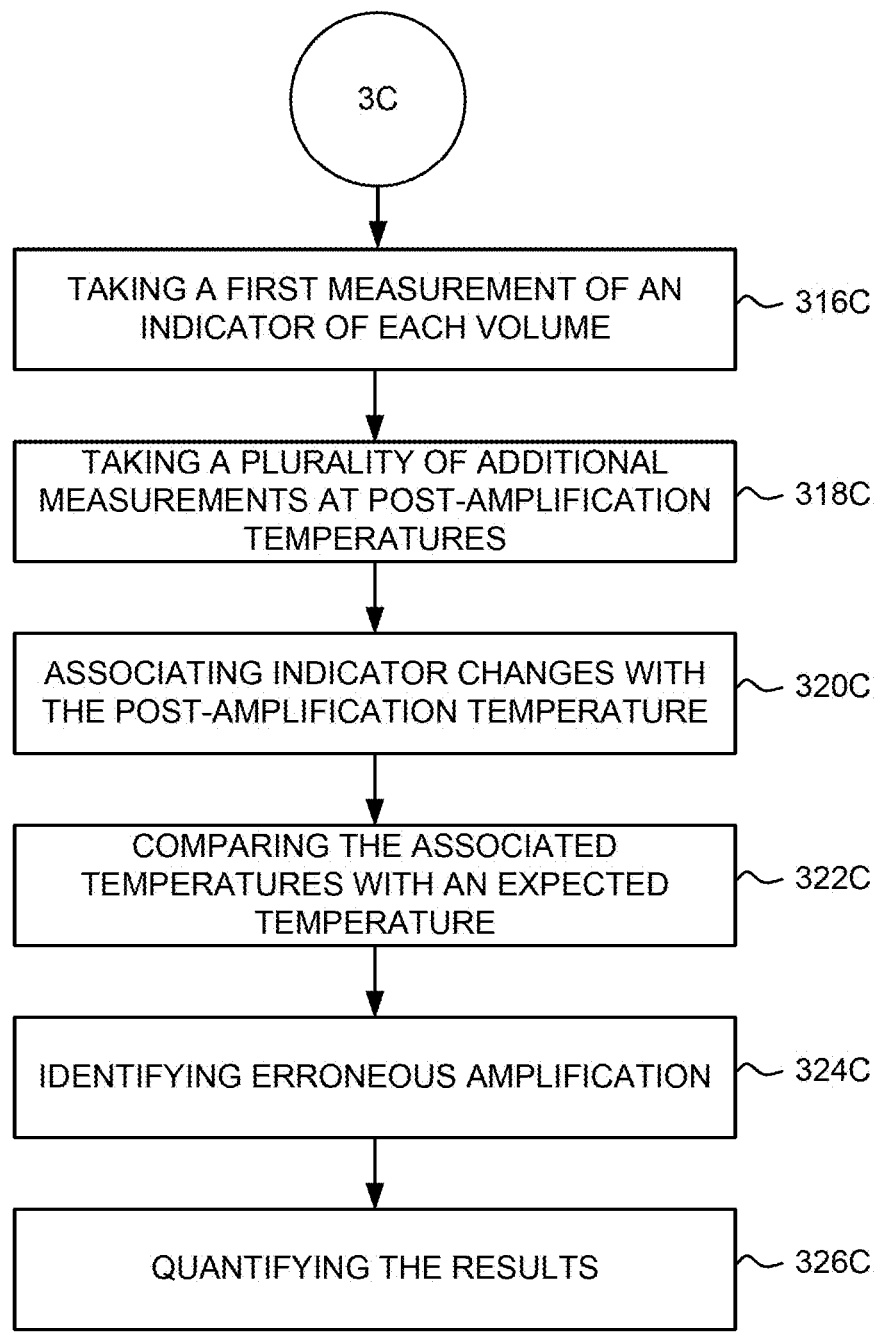

In one embodiment, the method of FIG. 3A may progress to 316C of FIG. 3C, where a melt stage may be used to quantify target nucleic acid amplification. For example, one or more of detection point 106, detection points 108, and detection points 110 of FIG. 1B may illustrate detection schemes for detecting an indicator of amplification, and this detection may be used to quantify the amplification of the target nucleic acid.

Figure 3D:
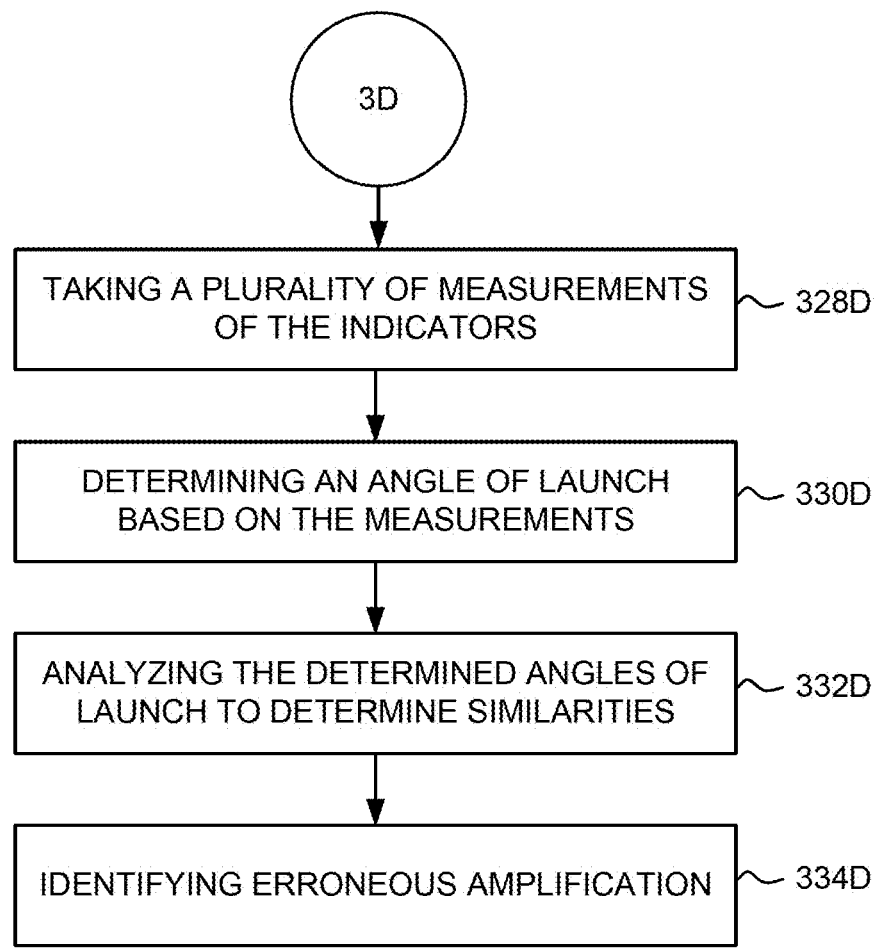

In one embodiment, the method of FIG. 3A may progress to 328D of FIG. 3D, where an angle of launch may be used to quantify target nucleic acid amplification. For example, one or more of detection point 106, detection points 108, and detection points 110 of FIG. 1B may illustrate detection schemes for detecting an indicator of amplification, and this detection may be used to quantify the amplification of the target nucleic acid.

FIG. 3B illustrates exemplary elements for a real time detection scheme of an indicator of amplification during digital amplification (e.g., dPCR assay). At 306B, a plurality of measurements of an indicator of amplification may be taken for each of the plurality of sample reaction volumes at a predetermined amplification assay temperature while subjecting the reaction volumes to the amplification assay. For example, the indicator of amplification exhibited by a reaction volume may indicate the presence of amplified product (e.g., amplification of the target nucleic acid molecule).

Figure 5:
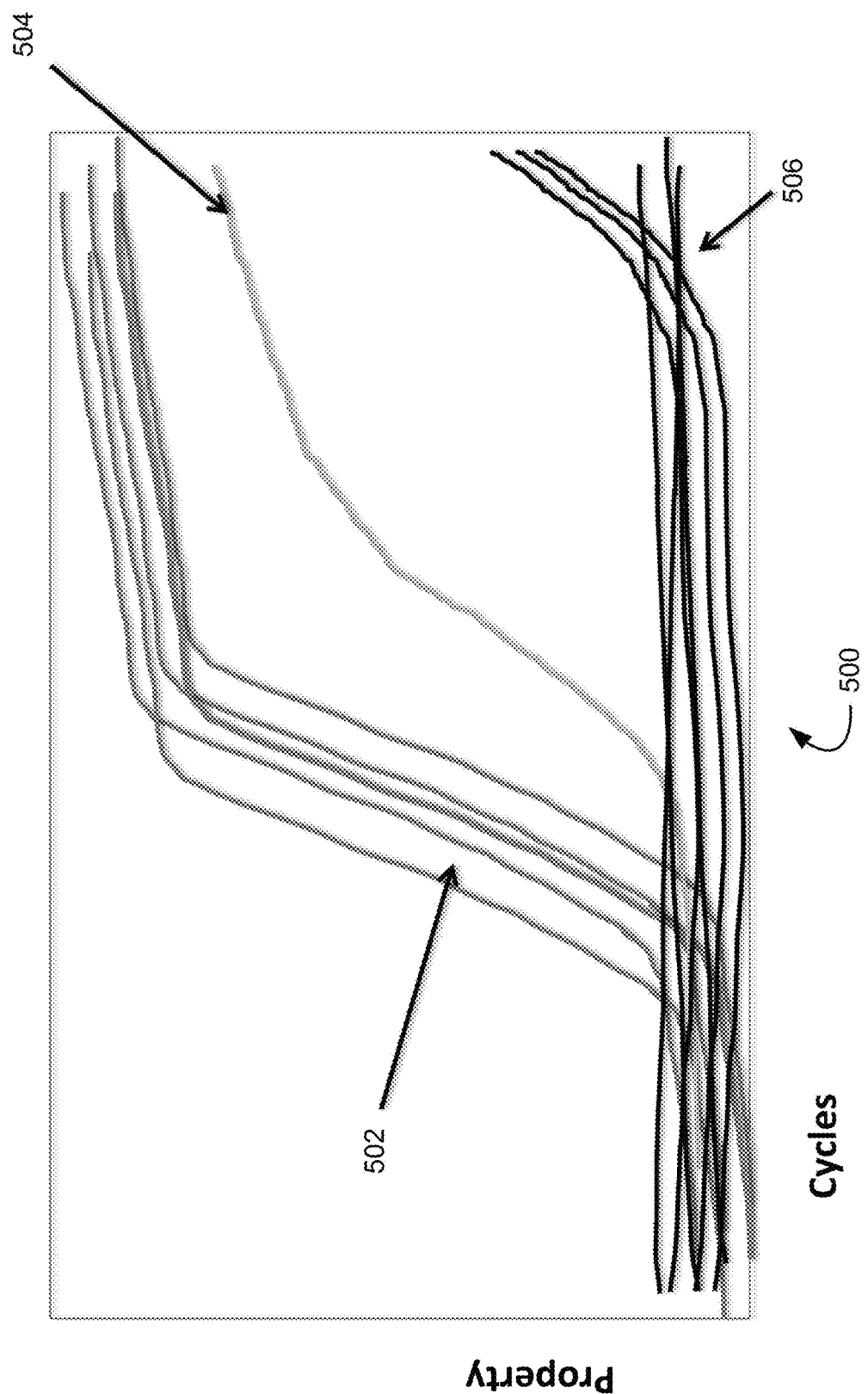
FIG. 5 illustrates a graph of illustrative, prophetic exemplary real time amplification detection measurements.

In an embodiment, one or more dyes may be used that fluoresce when bound to double-stranded nucleic acids, and this fluorescence may be detected as an indicator of amplification. For example, the nucleic acid binding agent (dye) may produce a detectable signal when bound to double-stranded nucleic acids that is distinguishable from the signal produced when that same agent is in solution or bound to a single-stranded nucleic acid. The fluorescence may be detected using a fluorescence detector, for example mounted over a chip that houses the segregated sample reaction volumes, or may be detected in any other suitable manner. In an embodiment, the plurality of sample reaction volumes subjected to the amplification assay may be further subjected to a plurality or PCR steps, such as thermal cycling, as described herein. In one exemplary embodiment, the plurality of measurements may be taken during each PCR cycle at the predetermined amplification assay temperature. FIG. 5 illustrates a graph of illustrative, prophetic exemplary measurement results for the indicator of amplification. The measured indicator of amplification for the plurality of sample reaction volumes is represented by the "Property" attribute on the y-axis and the PCR thermal cycles are represented on the x-axis.

Referring again to FIG. 3B, at 308B, quantification cycle (Cq) or cycle threshold (Ct) values may be determined for the plurality of sample reaction volumes based on the obtained measurements. A Cq value may be the cycle in which an indicator of amplification can be measured and Ct value may be the value at which the measured indicator of amplification reaches a threshold value (e.g., predetermined threshold value). For example, with reference to FIG. 5, reaction volumes represented by the lines 502 have approximately the same Ct values. Line 504 represents reaction volumes with a later Ct value, and lines 506 represent additional reaction volumes with the latest Ct values. In an embodiment, the Cq values (e.g., measured indicator values at a cycle) may be determined at each cycle at a predetermined point during the cycle, at a plurality of predetermined cycles, or based on any suitable period.

In embodiments that leverage a multiplexing assay, reagents may be implemented that exhibit multiple indicators of amplification. For example, a multiplexing assay may include two probes, such as a FAM™ dye-labeled probe and a VIC® dye-labeled probe, and each probe may designed to exhibit an indicator of amplification based on one of a plurality of target nucleic acids. In some embodiments, an indicator of amplification based on the FAM dye-labeled probe may fluoresce at a different wavelength than an indicator of amplification based on the VIC dye-labeled probe. Accordingly, measured indicators (e.g., fluorescence) may be associated with a particular target nucleic acid based on the wavelength emitted. In these embodiments, measured Cq or Ct values may be attributed to a particular target nucleic acid based on the wavelength for the measured indicator.

At 310B, the determined Cq or Ct values may be compared to an expected Cq or Ct value. For example, based on the particular amplification assay implemented and the target nucleic acid, an expected Cq value or expected Ct value may be determined. The Cq or Ct values determined for the indicators exhibited by the reaction volumes based on the measurements taken may be compared to the expected CQ or Ct value.

In embodiments that leverage multiple indicators of amplification, determined Cq or Ct values may be associated with particular target nucleic acids, and the comparison may include comparing associated Cq or Ct values with expected Cq or Ct values for the associated target nucleic acid. For example, a first target nucleic acid may be associated with an indicator of amplification that fluoresces at a first wave length and a second target nucleic acid may be associated with an indicator of amplification that fluoresces at a second wave length. Cq or Ct values for each target nucleic acid may be determined based on fluorescence at each wave length, and the determined Cq or Ct values may be compared to expected Cq or Ct values for the target nucleic acid associated with the determined values. At step 312B, erroneous amplification may be detected based on the comparisons. For example, the expected Ct value may match (or substantially match) the Ct value for the indicators exhibited by the reaction volumes represented by lines 502. Accordingly, the measured indicator of amplification for the reaction volumes represented by lines 502 may indicate amplification of target nucleic acids. On the other hand, the Ct values for reaction volumes represented by lines 504 and 506 do not match the expected Ct value. Accordingly, the measured indicator of amplification for the reaction volumes represented by lines 504 and 506 indicates amplification of something other than the target nucleic acid or detection of amplification that is triggered by some other source (e.g., primer dimer, dust, misincorporation, or any other suitable source) and not by actual detection of amplified target nucleic acids. Comparison of determined Cq values and expected Cq values may be similarly implemented to detect erroneous amplification.

In embodiments that leverage multiple indicators of amplification, Ct or Cq values associated with a particular target nucleic acid (e.g., based on the wavelength for indicators measured to determine the Ct or Cq values) may be used to detect erroneous amplification. For example, a first set of Ct or Cq values may be associated with a first target nucleic acid and a second set of Ct or Cq values may be associated with a second target nucleic. A comparison between the first set of Ct or Cq values and the expected Ct or Cq values for the first target nucleic acid may be used to detect erroneous amplification measured as a result of indicators of amplification associated with the first target nucleic acid (e.g., based on a wavelength). Similarly, a comparison between the second set of Ct or Cq values and the expected Ct or Cq values for the second target nucleic acid may be used to detect erroneous amplification measured as a result of indicators of amplification associated with the second target nucleic acid. Thus, depending on the wavelength for an exhibited indicator, a comparison may be made to one of the expected Ct or Cq values to identify erroneous amplification (or an indicator exhibited based on something other than amplified target nucleic acid).

As 314B in FIG. 3B, the amplified product of the target nucleic acid resulting from the amplification process may be quantified. For example, the amount of amplification may be directly proportional to the measured indicator of amplification for the reaction volumes that comprised a Cq or Ct value substantially similar to the expected Cq or Ct value. In an embodiment, the quantification also may be based on identification of the measured indicator of amplification triggered by a source other than target nucleic acid amplification. For example, reaction volumes that comprise a Cq or Ct value that do not substantially match the expected Cq or Ct value may include a measured indicator of amplification that corresponds to sources other than target nucleic acid amplification. Accordingly, the measured indicator of amplification for these reaction volumes may be discounted when quantifying the amplification for the target nucleic acid.

In embodiments that leverage a multiplexing assay, amplified product of each of a plurality of target nucleic acids may be quantified. For example, the amount of amplified product for a first target nucleic acid may be directly proportional to the measured indicators of amplification associated with the first target nucleic acid that comprised a Cq or Ct value substantially similar to the expected Cq or Ct value for the first target nucleic acid. An amount of amplified product for a second target nucleic acid may be similarly quantified. Indicators exhibited by reaction volumes that do not substantially match the expected Cq or Ct values for either of the target nucleic acids may include measured indicators of amplification that correspond to sources other than target nucleic acid amplification.

In an embodiment, measured indicators of amplification for the reaction volumes that included a Cq or Ct value substantially similar to the expected Cq or Ct value (for at least one target nucleic acid) may confirm expected amplification, and amplification of the target nucleic acid may be quantified based on these confirmed indicators. For example, a Poisson model may be used along with a total number of sample reaction volumes and total number of non-amplifying sample reaction volumes, distinguished using Cq or Ct value substantially similar to the expected Cq or Ct value, to calculate a mean number of reactions per sample reaction volume. The result can be divided by the mean volume of each sample reaction volume to arrive at the copies per unit volume for the reaction product that includes a Cq or Ct value substantially similar to the expected Cq or Ct value.

FIG. 3C illustrates an exemplary method that utilizes a melt stage and detection of an indicator of post digital amplification. At 316C, after subjecting the reaction volumes to the amplification assay, a set of first measurements of an indicator of amplification may be taken for each of the plurality of sample reaction volumes at a first temperature. In an embodiment, the measurement of the indicator of amplification may be taken for each of the plurality of sample reaction volumes at a first temperature post-amplification (e.g., ambient temperature). For example, the set of first measurements may comprise end point detection 102 of FIG. 1B, taken at ambient temperature after performance of an amplification assay.

In an embodiment, the indicator of amplification measured may be based on an intercalating dye (e.g., SYBR® dye) that binds to double stranded nucleic acids, as described herein. In some embodiments, the indicators measured for real time detection of amplified nucleic acids (e.g., based on Cq or Ct values or based on angle of launch analysis) may be different from the indicators measured for the melt stage analysis. For example, the real time detection techniques may leverage a non-intercalating dye or probe based indicators that are not useful to a melt analysis. In other embodiments, the indicator measured may be consistent throughout the various detection techniques.

At 318C, at least one set of additional measurements may be taken of the indicator of amplification at a post-amplification temperature that is higher than the first temperature. For example, an initial measurement of the indicator of amplification may include measuring the properties of sample reaction volumes while the volumes are at a first temperature (e.g., ambient temperature) after amplification (e.g., PCR amplification). FIG. 4 illustrates a graph of illustrative, prophetic exemplary detection results. The indicator of amplification (e.g., fluorescence) for the sample reaction volumes may be represented by the "Property" attribute on the y-axis and the temperature may be represented by the x-axis. Accordingly, the measured indicator of amplification for the plurality of reaction volumes measured at an ambient temperature is illustrated in the graph of FIG. 4.

In an embodiment, the sample reaction volumes may be heated at a constant rate over a period of time, such as 10 minutes, 15 minutes, 30 minutes, 1 hour, or any other suitable period of time. During the heating, the indicator of amplification exhibited by the plurality of sample reaction volumes may be measured at least once, and, in some embodiment, a plurality of times.

In an embodiment, indicator of amplification (e.g., fluorescence) exhibited by the plurality of sample reaction volumes may be measured at a series of intervals during the heating. For example, FIG. 4 illustrates a graph of illustrative, prophetic exemplary detection results, where the indicator of amplification may be measured at various target temperatures. In an embodiment, the target temperatures may be based on temperature intervals (e.g., 5° C., 10° C., and the like), or may include a predetermined set of target temperatures. At each target temperature, the indicator of amplification may be measured such that changes in the indicator may be identified.

In an embodiment, the indicator of amplification exhibited by the plurality of sample reaction volumes may be measured rapidly at closely spaced intervals during the heating. In analyzing the rapidly measured property, trends for the indicator of amplification exhibited by the plurality of reaction volumes may be determined. For example, the analysis may show a trend that a set of sample reaction volumes from the plurality of reaction volumes exhibits a decrease in the indicator of amplification as the temperature increases. The trends may be similar to results determined from comparisons during interval detection during the temperature increase.

In an embodiment, the rapid detection may enable identification of trends at specific temperatures (e.g., temperatures other than the target temperatures of the interval detection). For example, a temperature (or temperature window) may trigger a noticeable change (e.g., change beyond a threshold) in the indicator of amplification exhibited by some of the reaction volumes. The rapid detection may enable identification of these temperatures, or temperature windows, via analysis of the changes in the indicator of amplification. Accordingly, the rapid detection methodology may provide enhanced sensitivity to the analysis.

At 320C, identified changes in the indicator of amplification may be associated with the post-amplification temperature for the change. For example, referring again to FIG. 4, identified change 404 may be associated with the temperature 75° C. and identified change 408 may be associated with the temperature 85° C. Identified changes 402 may comprise multiple changes, and each change may be associated with one of temperature 55° C. and 65° C., as illustrated.

In an embodiment, during heating, measurement of the indicator of amplification may occur rapidly. Similar to the interval detection analysis, the identified changes to measured indicator of amplification for the plurality of reaction volumes at various temperatures may be associated with each temperature for the change.

At 322C, the associated temperatures may be compared to an expected melt temperature. For example, based on the particular amplification assay implemented and the target nucleic acid, an expected melt temperature (or expected melt temperature range) may be predetermined such that the target nucleic acid would be expected to melt at the temperature. The associated temperatures for changes in the indicator of amplification based on the measurements taken may be compared to the expected melt temperature.

At 324C, erroneous amplification may be identified based on the comparisons. In an embodiment, the identified changes in the indicator of amplification for the plurality of reaction volumes may be analyzed to determine changes triggered by a source other than amplification of the target nucleic acid. A change in the indicator of amplification exhibited by a reaction volume based on amplification of the target nucleic acid would be expected to decrease at the expected melt temperature or temperature range (e.g., fluorescence exhibited by a reaction volume would be expected to decrease at the expected melt temperature). For example, the expected melt temperature for the target nucleic acid here may be 70° C., or an expected melt temperature range may be from 65° C. to 75° C.

In an embodiment, a single point detection algorithm may be used with the endpoint detection (e.g., at ambient temperature), as illustrated by detection point 106 of FIG. 1B. For example, an identified change may be determined based on the detection results at ambient temperature (e.g., detection point 102) and the predetermined temperature for single point detection (e.g., detection point 106). One of identified changes 402 may comprise the identified change based on the single point detection.

For example, the detected change at these temperatures may include a further separation of the reaction volumes that exhibit indicators of amplification triggered by nucleic acid amplification from the reaction volumes that do not. Reaction volumes that exhibit some indicator of amplification may show a decrease such that the background noise of the results is reduced. For example, when a dye, such a SYBR dye (or other intercalating dye), is used to produce the indicator of amplification, the dye may bond with various reaction products (e.g., nucleic acids) due to the non-specific design of the dye. Accordingly, background noise (e.g., fluorescence) may be caused by reaction products bonding to a non-specific dye. In an embodiment, reaction volumes that exhibit the indicator of amplification may be discernible from reaction volumes that do not based on the further separation, and the amplification of the target nucleic acid may be more accurately quantified based on the discerned reaction volumes.

In an embodiment, an interval detection algorithm may be used with the endpoint detection (e.g., at ambient temperature), as illustrated by detection points 108 of FIG. 1B. For example, identified changes may be determined based on the detection results at ambient temperature (e.g., detection point 102) and the predetermined temperatures for interval detection (e.g., detection points 108). FIG. 4 may illustrate changes 402 (as discussed above), 404, and 406 based on interval detection.

Identified change 404, associated with temperature 75° C., may indicate changes to indicators triggered by amplification of the target nucleic acid. Because the expected melt temperature for the target nucleic acid comprises 70° C., or a range between 65° C. to 75° C., the decrease of the exhibited indicator detected at 75° C. correspond to indicator triggered by amplification of the target nucleic acid. Identified change 408, associated with temperature 85° C., may indicate changes to indicators triggered by a source other than amplification of the target nucleic acid. Because the expected melt temperature for the target nucleic acid comprises 70° C., or a range between 65° C. to 75° C., the changes detected at 85° C. correspond to indicators triggered by other sources. Indicators of amplification 410, measured at temperature 95° C., also corresponds to indicators triggered by a source other than amplification of the target nucleic acid. At such a high temperature, nucleic acids would be expected to melt, and therefore indicators 410 may correspond to a source like dust, or some other source that may cause the indicator to persist above certain temperature thresholds.

In an embodiment, during heating, indicator measurement may occur rapidly in lieu of or in addition to set temperature point interval measurement. For example, rapid measurement algorithm may be used with the endpoint measurement (e.g., at ambient temperature), as illustrated by detection points 110 of FIG. 1B. Identified changes may be determined based on the detection results at ambient temperature (e.g., detection point 102) and rapidly over the melt temperatures (e.g., detection points 110).

For example, changes in the indicators (e.g., decreases) at temperatures other than the expected melt temperature (or expected melt temperature range) for the target nucleic acid may correspond to sources other than target nucleic acid amplification (e.g., indicators triggered by something other than target nucleic acid amplification). On the other hand, changes to indicators (e.g., decreases) at the expected melt temperature (or expected melt temperature range) for the target nucleic acid may correspond to target nucleic acid amplification (e.g., indicators triggered by target nucleic acid amplification).

As 326C, the amount of amplified product of the target nucleic acid resulting from the amplification process may be quantified. For example, indicators exhibited by the reaction volumes at ambient temperature may suggest a level of amplification that occurred in each reaction volume, however not all of the amplification may comprise the target nucleic acid. In other words, the indicators of amplification presented by the reaction volumes at ambient temperature may indicate amplification of something other than the target nucleic acid, or may be triggered by some other source. These may comprise, for instance, primer dimer, misincorporation, dust, or any other suitable source. Performance of the heating and a subsequent analysis of the measured property may enable identification of indicators that are not the results of amplification of the target nucleic acid. After considering the indicators that are related to some other source, the amplification for the target nucleic acid may be quantified with greater accuracy.

In an embodiment, the identified changes in the indicators for the plurality of reaction volumes may be analyzed to determine indicators triggered by a source other than amplification of the target nucleic acid. For example, based on the particular target nucleic acid, an expected melt temperature (or expected melt temperature range) may be determined such that the target nucleic acid would be expected to melt at the temperature. Therefore, an indicator exhibited by a reaction volume based on amplification of the target nucleic acid would be expected to decrease at the expected melt temperature or temperature range (e.g., fluorescence exhibited by a reaction volume would be expected to decrease at the expected melt temperature).

In an embodiment, the amplification may be directly proportional to the change detected to indicators (e.g., detected decrease in fluorescence) at the expected melt temperature (or expected melt temperature range). In an embodiment, the quantification may also be based on identification of indicators triggered by a source other than target nucleic acid amplification. For example, it may be determined that indicators of amplification that changed (e.g., decreased) at temperatures other than the expected melt temperature (or expected melt temperature range) correspond to sources other than target nucleic acid amplification. Accordingly, these indicators may be discounted when quantifying the amplification for the target nucleic acid.

In an embodiment, clustering of measured melt temperatures may be used to identify target nucleic acid amplification and quantify amplified target nucleic acids. For example, decreases to a plurality of indicators of amplification associated with a plurality of sample reaction volumes may be measured at a particular temperature (or within a temperature range) to determine melt temperatures for these indicators, as described herein. These measured melt temperatures may be clustered, for example, based on calculated Euclidean distances and/or calculated silhouette values such that clusters of indicators with similar melt temperatures may be determined. Reference is made to *HRM Experiments, Using MeltDoctor™ HRM Reagents and High Resolution Melt Software v3.0*, Life Technologies, 2010, which reviews the use of silhouette scores for clustering when performing a melt using available software tools. Those of ordinary skill in the art will recognize various additional techniques exist for clustering data that may be implemented to obtain clusters for the purposes of the present embodiments. Accordingly, one or more clusters may be identified that comprise indicators of amplification with similar melt temperatures.

In some embodiments, an indicator of amplification may be confirmed as indicating target nucleic acid amplification when the indicator is determined to be within an identified cluster of melt temperatures. For example, a first identified cluster may be associated with a first target nucleic acid based on a comparison between the measured melt temperature (or melt temperature range) for the identified cluster and the expected melt temperature for the first target nucleic acid. Similarly, a second identified cluster may be associated with a second target nucleic acid based on a comparison between the measured melt temperature (or melt temperature range) for the identified cluster and the expected melt temperature for the second target nucleic acid. In such an embodiment, indicators may be confirmed for each target nucleic acid based on the identified melt temperature cluster for the indicators. In some embodiments, it may be determined that indicators that are not within one of the identified clusters do not comprise amplified target nucleic acid. Accordingly, these indicators may be discounted when quantifying the amplification of the target nucleic acids.

In an embodiment, amplification of each target nucleic acid may be quantified based on indicators of amplification confirmed by clustering for each target nucleic acid, as described herein, or indicators of amplification confirmed based on an expected melt temperature (or an expected melt temperature range) for each target nucleic acid. For example, a Poisson model may be used along with a total number of sample reaction volumes and total number of non-amplifying sample reaction volumes, distinguished using indicators changes at an expected melt temperature or indicators that are not part of a cluster, to calculate a mean number of reactions per sample reaction volume. The result can be divided by the mean volume of each sample reaction volume to arrive at the copies per unit volume for the reaction product melting at the expected melt temperature or temperature range.

FIG. 3D illustrates exemplary elements for an angle of launch detection scheme to identify amplification during digital amplification. At 328D, a plurality of measurements of an indicator of amplification may be taken for each of the plurality of sample reaction volumes at a predetermined amplification assay temperature while subjecting the sample reaction volumes to the amplification assay. For example, the indicator of amplification exhibited by a sample reaction volume may indicate the presence of amplified product (e.g., amplification of the target nucleic acid molecule).

In an embodiment, the plurality of measurements of an indicator of amplification taken for each of the plurality of sample reaction volumes may be performed similarly to 306B of FIG. 3B. For example, one or more dyes and/or probes may be used that fluoresce when bound to double-stranded nucleic acids, and this fluorescence may be detected as an indicator of amplification. The fluorescence may be detected using a fluorescence detector angled to detect fluorescence from the segregated reaction volumes. In an embodiment, the plurality of reaction volumes subjected to the amplification assay may be further subjected to a plurality of PCR steps, such as thermal cycling, as described herein. In one exemplary embodiment, the plurality of measurements may be taken during each thermal cycle at a predetermined amplification assay temperature.

Figure 6B:
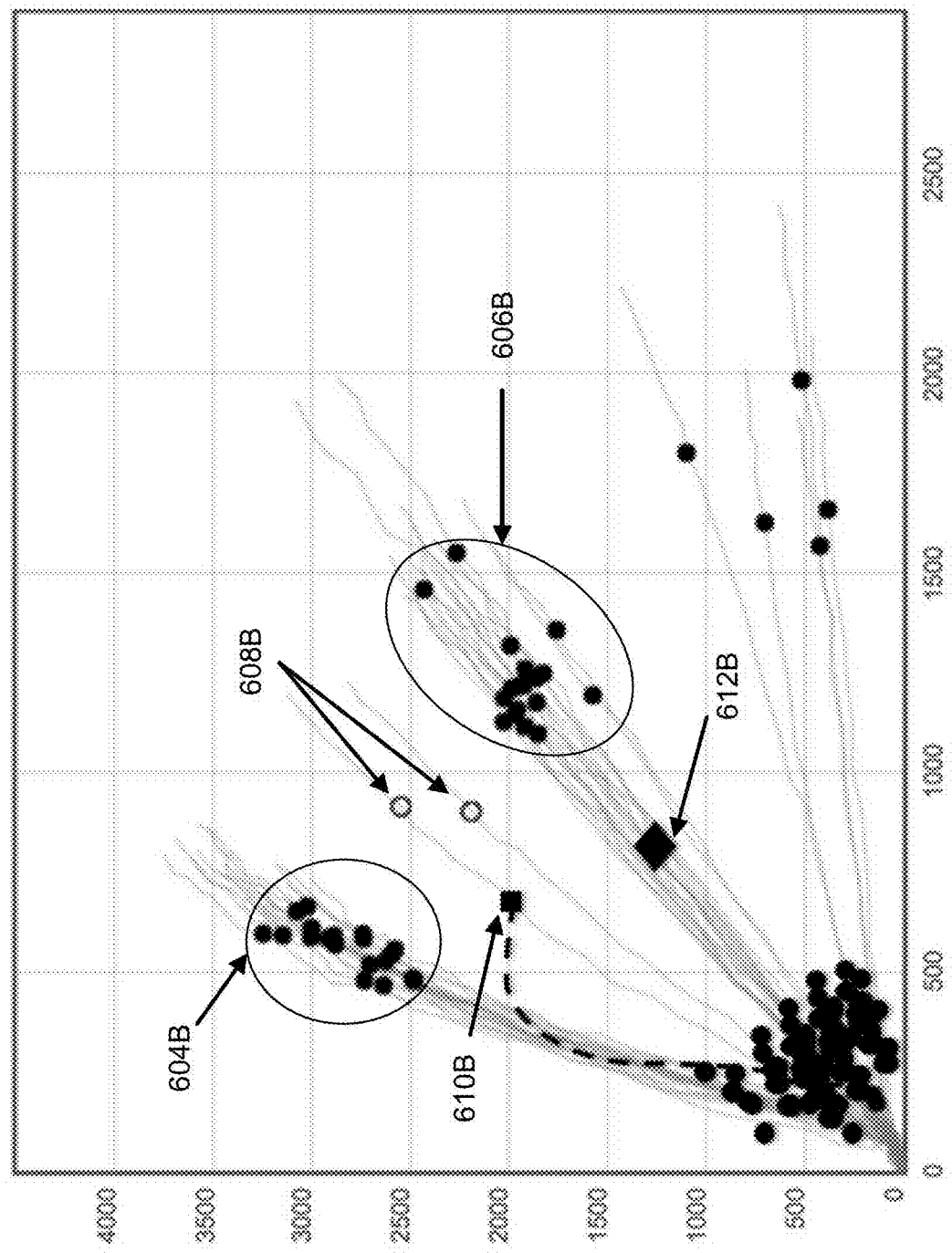

FIGS. 6A and 6B illustrate graphs of illustrative, prophetic exemplary measurement results for the indicator of amplification. Graphs 600A and 600B illustrate angle of launch analysis based on the plurality of measurements at different cycle numbers during amplification. In an embodiment, the measurements may be taken at each cycle at a predetermined point during the cycle, at a plurality of predetermined cycles, or based on any suitable period.

In some embodiments, a sample reaction volume may exhibit multiple indicators of amplification. For example, multiples dyes and/or probes may be implemented such that a sample reaction volume exhibits one or more indicators based on the amplification reactions occurring in the sample reaction volume. In some embodiments, a first indicator may indicate amplification of a first target nucleic acid while a second indicator may indicate amplification of a second target nucleic acid. For instance, Graphs 600A and 600B may illustrate amplification results for reactions that leverage two probes (e.g., FAM™ and VIC® probes), or any other suitable probes and/or dyes. Here, measured indicators of amplification based on a first of the probes are shown on the x-axis and measured indicators of amplification for a second of the probes are shown on the y-axis. In an embodiment, the first probe may be designed to amplify a first target nucleic acid while the second probe may be designed to amplify a second target nucleic acid.

In an embodiment where the plurality of measurements were previously taken, for instance an embodiment where the method of FIG. 3B is performed prior to the method of FIG. 3D, step 328D may be omitted. For example, data for the plurality of measurements may be available based on the measurements taken during the method of FIG. 3B, and thus the data may be analyzed, as described herein, without need for obtaining additional measurements.

Referring again to FIG. 3D, at 330D, an angle of launch for measured indicators of each of the plurality of sample reaction volumes may be determined based on the measurements taken at various cycles. For example, graph 600A of FIG. 6A illustrates measurement values for indicators of amplification taken at a first cycle during the amplification process and graph 600B of FIG. 6B illustrates measurement values for indicators of amplification taken at a second cycle during the amplification process, where the second cycle is some time after the first cycle. In an embodiment, the first cycle may be at cycle 27 of the amplification process and the second cycle may be at cycle 40 of the amplification process.

In an embodiment, for each cycle at which measurements were taken (e.g., at 328D or any previous elements in FIG. 3D at which real time measurements were taken) values may be stored for the indicator measurement values of each of the plurality of sample reaction volumes at that cycle. Here, the measurements taken at cycle 27 are illustrated in graph 600A of FIG. 6A and the measurements taken a cycle 40 are illustrated in graph 600B of FIG. 6B.

The measurements at each measured cycle may be analyzed to determine the angle of launch (or trajectory) for each reaction volume. For instance, a measured data point associated with a reaction volume at a given measured cycle may be compared to a reference point (e.g., origin point (0,0)) such that an angle may be determined. In some embodiments, the particular angles for given data points may be determined based on the $\tan^{-1}$ function and the x and y values for the data point. Over the duration of amplification (e.g., over the totality of cycles or up to a predetermined cycle), the angles determined at each measured cycle for each reaction volume (e.g., each data point) may be averaged (or smoothed) such that an angle of launch may be determined for indicators measured from the individual reaction volumes. In some embodiments, a slope for the angles of launch determined for the given reaction volumes may be calculated using a regression analysis or by some other suitable manner.

In an embodiment, graph 600A of FIG. 6A illustrates exemplary measured values 602A for the plurality of sample reaction volumes at cycle 27. In this example, the measured values for indicators of amplification have not separated such that the values may be distinguished or such that the angles of launch determined for sample reaction volumes may be distinguished. In an embodiment, graph 600B of FIG. 6B illustrates exemplary measured values for the plurality of sample reaction volumes at cycle 40. In this example, the indicators have separated such that the values may be distinguished or such that the angles of launch determined for sample reaction volumes may be distinguished. Accordingly, the sample reaction volumes associated with the illustrated data points in graphs 600A and 600B may comprise determined angles of launch.

Referring again to FIG. 3D, at 332D, the determined angles of launch may be analyzed to determine differences and similarities between the plurality of sample reaction volumes. In an embodiment, data points 604B in FIG. 6B may illustrate measurements taken for a plurality of sample reaction volumes that share a similar indicator measurement at cycle 40 and that share a similar determined angle of launch (e.g., based on the measurements taken at each measured cycle up to cycle 40). Similarly, data points 606B may illustrate measurements taken for a plurality of sample reaction volumes that share a similar indicator measurement at cycle 40 and that share a similar determined angle of launch. These data points may be clustered, as described herein or using known clustering algorithms, based on one or both of indicator measurements at cycle 40 and/or calculated angles of launch. In an embodiment, the angles of launch may be compared based on the calculated slopes, where angles may be declared similar when a calculated slope for a first angle of launch is within a threshold value of a calculated slope for a second angle of launch.

In an embodiment, the determined angles of launch and/or calculated slopes may confirm whether an indicator exhibited by a sample reaction volume corresponds to amplification of a first target nucleic acid, a second target nucleic acid, or both. For instance, in graphs 600A and 600B of FIGS. 6A and 6B measured indicators of amplification based on a first probe are shown on the x-axis and measured indicators of amplification based on a second probe are shown on the y-axis. In an embodiment, the first probe may be designed to amplify a first target nucleic acid while the second probe may be designed to amplify a second target nucleic acid. Thus, an angle of launch within a first range (e.g., approximately 60° to 90°) may confirm that a data point is based on amplification of the first target nucleic acid. Similarly, an angle of launch within a second range (e.g., approximately 0° to 30°) may confirm that a data point is based on amplification of the second target nucleic acid. An angle of launch within a third range (e.g., approximately 30° to 60°) may confirm that a data point is based on amplification of both the first target nucleic acid and the second target nucleic acid.

In some embodiments, the angle of launch analysis may flag the sample reaction volumes associated with these data points as containing validated target nucleic acid amplification for one or more target nucleic acids. For instance, sample reaction volumes associated with clustered data points 604B may be flagged as containing validated amplified first target nucleic acid based on the angle of launch for the cluster. Similarly, sample reaction volumes associated with clustered data points 604B may be flagged as containing validated amplified first target nucleic acid and amplified second target nucleic acid based on the angle of launch for the cluster.

Data points 608B may illustrate measurements taken for two sample reaction volumes that share a similar indicator measurement at cycle 40 and that share a similar determined angle of launch, however, these sample reaction volumes may not share these values with other sample reaction volumes. For instance, data points 604B and 606B each form a cluster, while data points 608B do not. In some examples, these values may indicate false indicators of amplification. For instance, the angle of launch analysis may flag the sample reaction volumes associated with these data points as containing off-target amplicons (amplicons that are something other than amplified target nucleic acid). Detection techniques as described with reference to FIGS. 3A-3C may be implemented with the angle of launch analysis to further confirm whether these sample reaction volumes contain off-target amplicons.

In an embodiment, data point 610B may illustrate a measurement taken for a sample reaction volume at cycle 40 that is not similar to other sample reaction volumes. For instance, the measurement value at cycle 40 for the sample reaction volume associated with data point 610B may be different from the measurement values at cycle 40 for the clusters of sample reaction volumes associated with data points 604B and 606B. However, the determined angle of launch for the reaction volume associated with data point 610B may be similar to the determined angles of launch for the cluster of sample reaction volumes associated with data points 604B. This determination may be based on compared slopes for the determined angles of launch, as described herein. In this embodiment, the similar angles of launch may indicate that the sample reaction volume associated with data point 610B contains amplified target nucleic acid consistent with the cluster of sample reaction volumes associated with data points 604B.

The difference between the measurements take at cycle 40 for these data points may be due to detection technique failures rather than amplification errors (e.g., off-target amplification). For instance, reagents used to produce the indicator of amplification may be present in low quantities, or other issues may be experienced by the amplification detection processes. In an embodiment, the angle of launch analysis may flag the sample reaction volume associated with data point 610B as containing validated target nucleic acid amplification consistent with the cluster of sample reaction volumes associated with data points 604B. Detection techniques as described with reference to FIGS. 3A-3C may be implemented with the angle of launch analysis to further confirm whether this sample reaction volume contains amplified target nucleic acid.

In an embodiment, data point 612B may also illustrate a measurement taken for a sample reaction volume at cycle 40 that is not similar to other sample reaction volumes. For instance, the measurement value at cycle 40 for the sample reaction volume associated with data point 612B may be different from the measurement values at cycle 40 for the clusters of sample reaction volumes associated with data points 604B and 606B. However, the determined angle of launch for the sample reaction volume associated with data point 612B may be similar to the determined angles of launch for the cluster of sample reaction volumes associated with data points 606B. In this embodiment, the shared angle of launch may indicate that the sample reaction volume associated with data point 612B contains amplified target nucleic acid consistent with the cluster of sample reaction volumes associated with data points 606B.

The difference between the measurements take at cycle 40 may also be due to detection technique failures rather than amplification errors (e.g., off-target amplification). The angle of launch analysis may flag the sample reaction volume associated with data point 612B as containing validated target nucleic acid amplification consistent with the cluster of sample reaction volumes associated with data points 606B. Detection techniques as described with reference to FIGS. 3A-3C may be implemented with the angle of launch analysis to further confirm whether this sample reaction volume contains amplified target nucleic acid.

Referring again to FIG. 3D, at 334D, erroneous amplification may be identified based on the determined angles of launch and additional amplification data. For example, data points 610B and 612B may each comprise conflicting factors as to whether the sample reaction volumes associated with the data points contain amplified target nucleic acid. For these data points, the clustering for measurements taken at cycle 40 may indicate erroneous amplification while the analyzed angle of launch may indicate on-target amplification (amplification of target nucleic acids). Here, additional data for the sample reaction volumes, such as Cq or Ct values as determined by the method of FIG. 3B or melt profile values as determined by the method of FIG. 3C, may be leveraged to determine whether the sample reaction volumes contain amplified target nucleic acid.

Figure 7A:
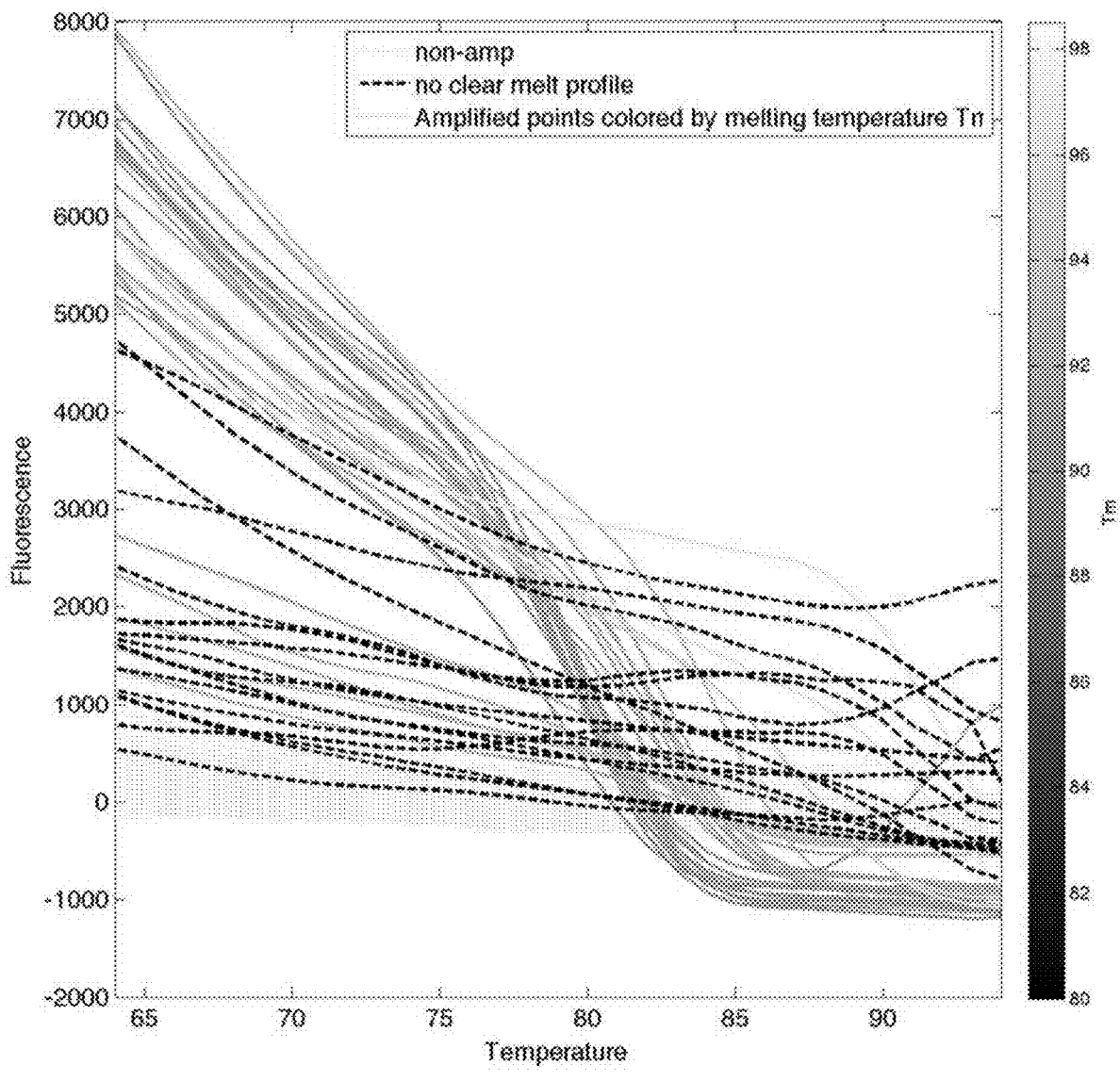
FIGS. 7A and 7B illustrate graphs of illustrative, prophetic exemplary melt stage detection measurements.
Figure 7B:
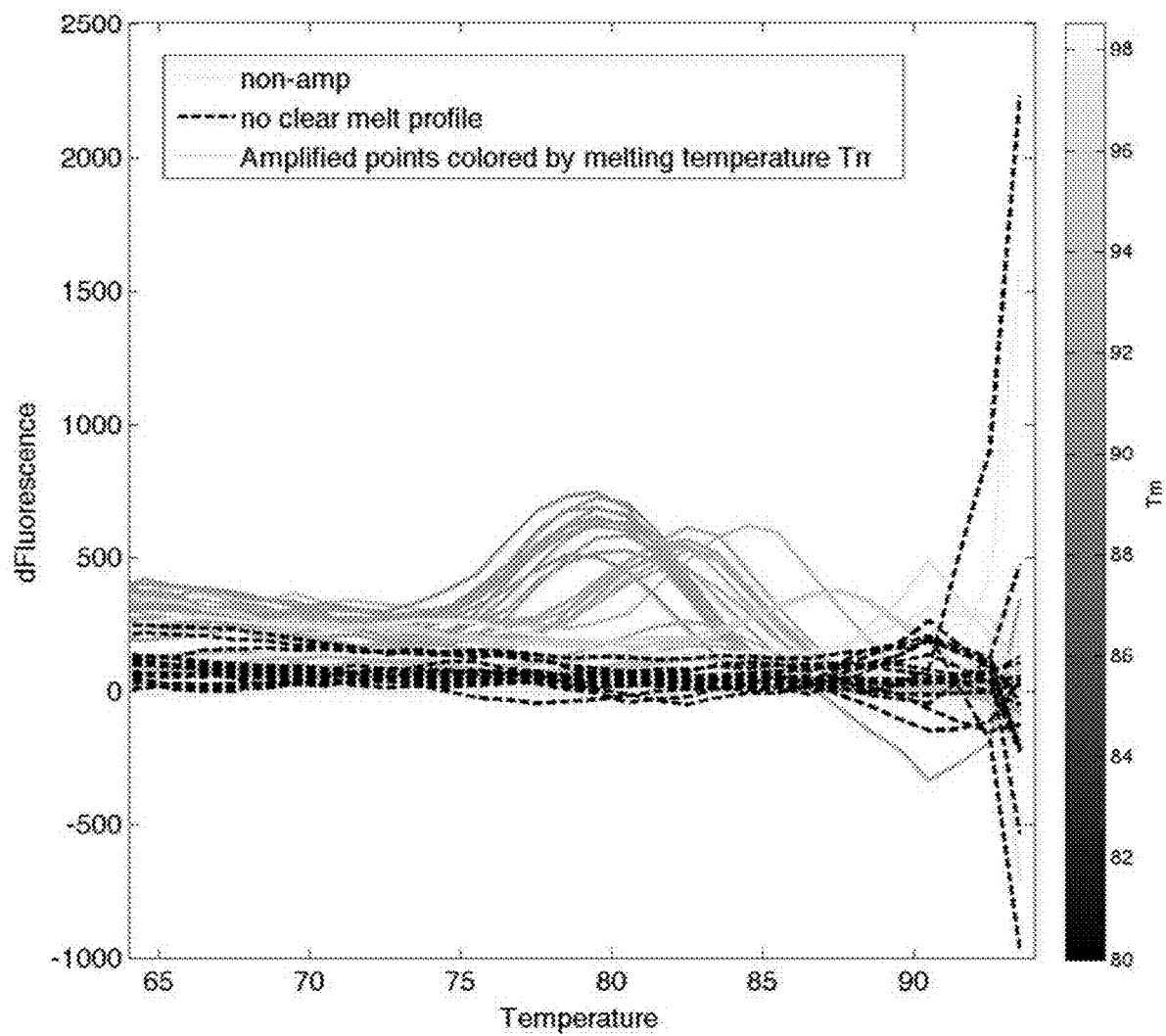

Graph 700A of FIG. 7A illustrates melt curves for a plurality of sample reaction volumes based on data derived from a melt technique, for instance a melt methodology as described in the method of FIG. 2A, 2B, or 3C. The line style depicts the class of the curves (e.g., amplified (solid), un-amplified (dotted), determined as questionable (dashed)), based on the identification technique described herein. Graph 700B of FIG. 7B illustrates a first derivate of the melt curves illustrated in graph 700A of FIG. 7A. Here, the line style also depicts the class of the curves (e.g., amplified (solid), un-amplified (dotted), determined as questionable (dashed)), based on the identification technique described herein, or other suitable identification techniques.

Figure 8:
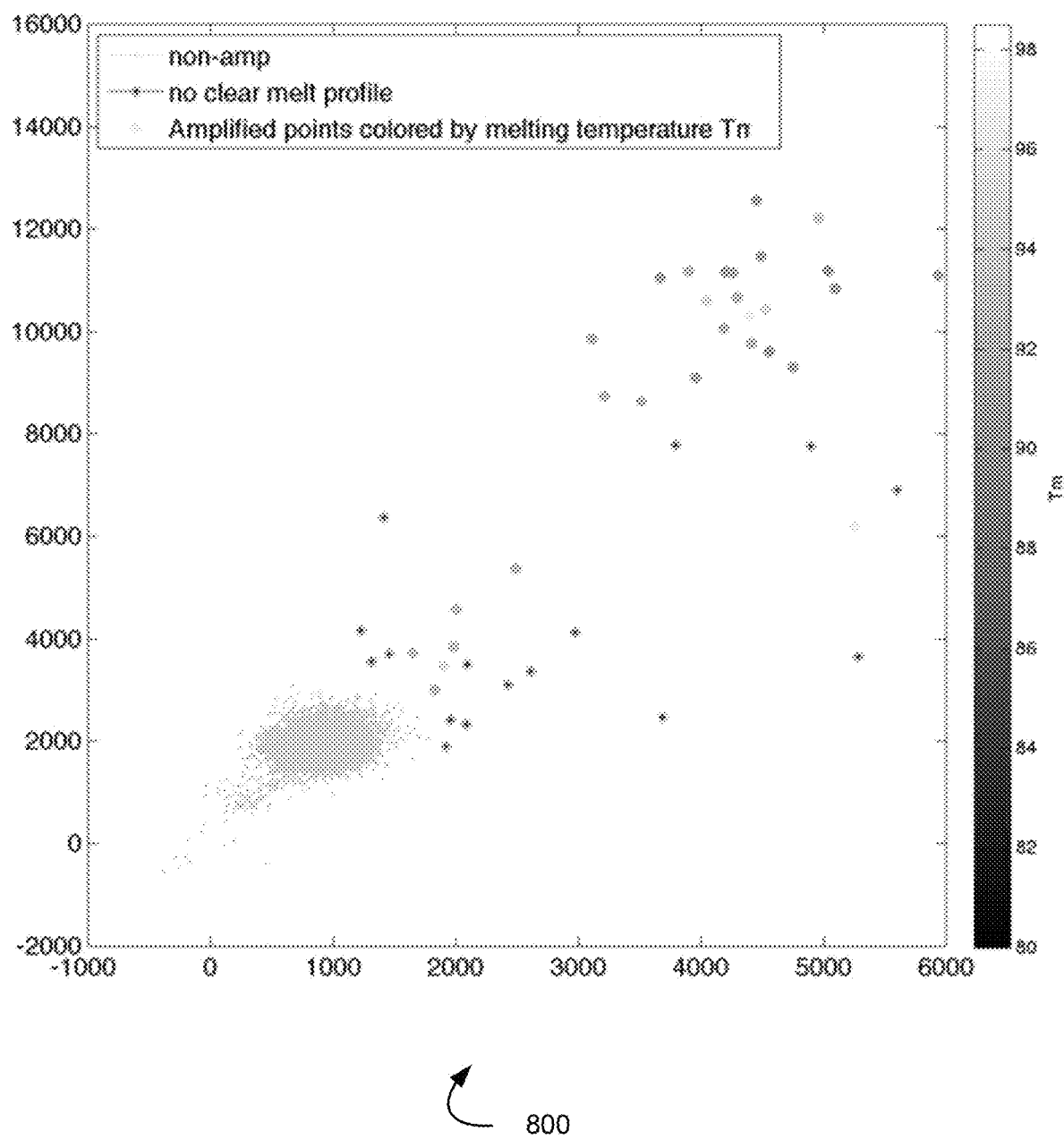
FIG. 8 illustrates a scatter plot of illustrative, prophetic exemplary melt stage detection measurements.

FIG. 8 illustrates a scatter plot of data points that depict values for measured indicators of amplification prior to the performance of a melt for a plurality of sample reaction volumes. In this visualization, the data points have been classified based on data from a melt detection technique. For instance, melt temperatures associated with the indicator of amplification exhibited by sample reaction volumes may be used to classify the associated data points. Here, the data points are classified as non-amplified (e.g., no or minimal detected indicator of amplification prior to melt and after amplification), no clear melt profile (e.g., the melt based technique did not identify a clear melt temperature), and shade based melt temperature (e.g., melt temperature for the measured indicator exhibited by a sample reaction volume associated with a data point corresponds to shade and accompanying temperature key).

In an embodiment, the identification from the melt curve analysis (e.g., as amplified, un-amplified, or questionable) may be used in combination with the angle of launch analysis to confirm whether a sample reaction volume contains amplified target nucleic acid or erroneous (or off-target) amplification (or emits an erroneous indicator of amplification). When combining an angle of launch detection technique with a melt detection technique, the confirmation may be based on the comparison between expected melt temperature and measured melt temperate for sample reaction volumes. For example, the identification based on the melt curve profiles for the sample reaction volumes associated with data points 610B and 612B of FIG. 6B may be used in order to confirm the amplification status of the sample reaction volumes.

In an embodiment, the identification from the real time detection technique, as described with reference to FIG. 3B, may be used in combination with the angle of launch analysis to determine whether a sample reaction volume contains amplified target nucleic acid or erroneous (or off-target) amplification (or emits an erroneous indicator of amplification). Here, the confirmation may be based on the comparison between expected Cq or Ct values and measured Cq or Ct values for a sample reaction volume. For example, the identification based on the expected Cq or Ct values and measured Cq or Ct values for the sample reaction volumes associated with data points 610B and 612B of FIG. 6B may be used in order to confirm the amplification status of the sample reaction volumes.

In an embodiment, the melt curve profile, the real time detection technique based on the expected Cq or Ct values, and detection technique based on a determined angle of launch may be used in combination in order to determine the amplification status of the sample reaction volumes. For example, combinations of two or more of these described techniques may be leveraged to arrive at an amplification status. In another embodiment, a sample reaction volume may be determined as containing amplified target nucleic acid when each of the detection techniques identifies the sample reaction volume as containing amplified target nucleic acid (e.g., all three techniques confirm that the sample reaction volume contains amplified target nucleic acid).

In embodiments where a multiplexing assay is implemented, confirmation may be specific to a particular target nucleic acid. For example, the melt curve profile, the real time detection technique based on the expected Cq or Ct values, and the detection technique based on a determined angle of launch may each correlate indicators of amplification to one of a plurality or target nucleic acids. Accordingly, a combination may be implemented to determine the amplification status of the sample reaction volumes and which particular amplified target nucleic acids are present (if any) in the sample reaction volumes.

In an exemplary embodiment, quantification of the target nucleic acid amplification may be based on both a real time detection method (as illustrated in FIG. 3B) and a melt detection technique (as illustrated in FIG. 3C). For example, quantification of a target nucleic acid may be based end point detection (as illustrated by detection point 102 of FIG. 1) and one or more of real time detection (as illustrated by detection points 104 of FIG. 1), single point detection (as illustrated by detection point 106 of FIG. 1), interval detection (as illustrated by detection points 108 of FIG. 1) and rapid detection (as illustrated by detection points 110 of FIG. 1). In exemplary embodiments, identification of erroneous amplification and accurate target nucleic acid amplification using real time detection techniques and/or melt stage techniques (as described with respect to FIGS. 3B and 3C) may each be used to quantify the amplification of a target nucleic acid. For example, based on the type of target nucleic acid being amplified, the amplification assay, the time/throughput desired for the analysis, and any other suitable consideration, a combination of end point analysis with one or more of the real time detection and melt stage may be selected.

In an embodiment, real time detection of an indicator of amplification during an amplification assay (as illustrated in FIG. 3) may also be used to determine a number of molecules present in a reaction volume prior to digital amplification. For example, based on the real time measurement of indicators of amplification for the plurality reaction volumes, it may be determined whether each reaction volume comprised zero, one, or more than one target nucleic acid molecule prior to dPCR amplification.

In some embodiments, combinations of dyes or probes may be used such that multiple indicators of amplification are exhibited by a sample reaction volume. For instance, a sample reaction volume may comprise detection reagents such that a first indicator of amplification may indicate amplification of a first target nucleic acid based on a first dye or probe, a second indicator of amplification (different from the first indicator of amplification) may indicate amplification of a second target nucleic acid based on a second dye or probe, and a third indicator of amplification (different from the first or second indicators of amplification) may indicate amplification of a third target nucleic acid based on a third dye or probe. In this example, particular indicators of amplification may be measured and analyzed based on the real time detection techniques, angle of launch detection techniques, and melt detection techniques described herein, such that quantification of amplified product for the individual first, second, and third target nucleic acids may be achieved.

In some embodiments, a first probe designed to indicate amplification of a first target nucleic acid and a second probe designed to indicate amplification of a second target nucleic acid may be implemented. The first and second indicators of amplification may be used as part of a real time detection technique (i.e., based on expected and measured Cq or Ct values) and/or angle of launch detection technique. In addition, a dye may be used along with the first and second probe such that a melt stage may be performed in order to implement a melt detection technique. Quantification of amplified product for the individual first and second target nucleic acids may be achieved using a combination of techniques.

In various embodiments, a sample holder may have a plurality of sample sites or volumes, configured for receiving a plurality of sample reaction volumes. Some examples of a sample holder may include, but are not limited to, a multi-well plate, such as a standard microtiter 96-well plate, a 384-well plate, a microcard, a through-hole array, or a substantially planar holder, such as a glass or plastic slide. The reaction sites in various embodiments of a sample holder may include depressions, indentations, ridges, through-holes, and combinations thereof, patterned in regular or irregular arrays formed on the surface of the sample holder.

Figure 9:
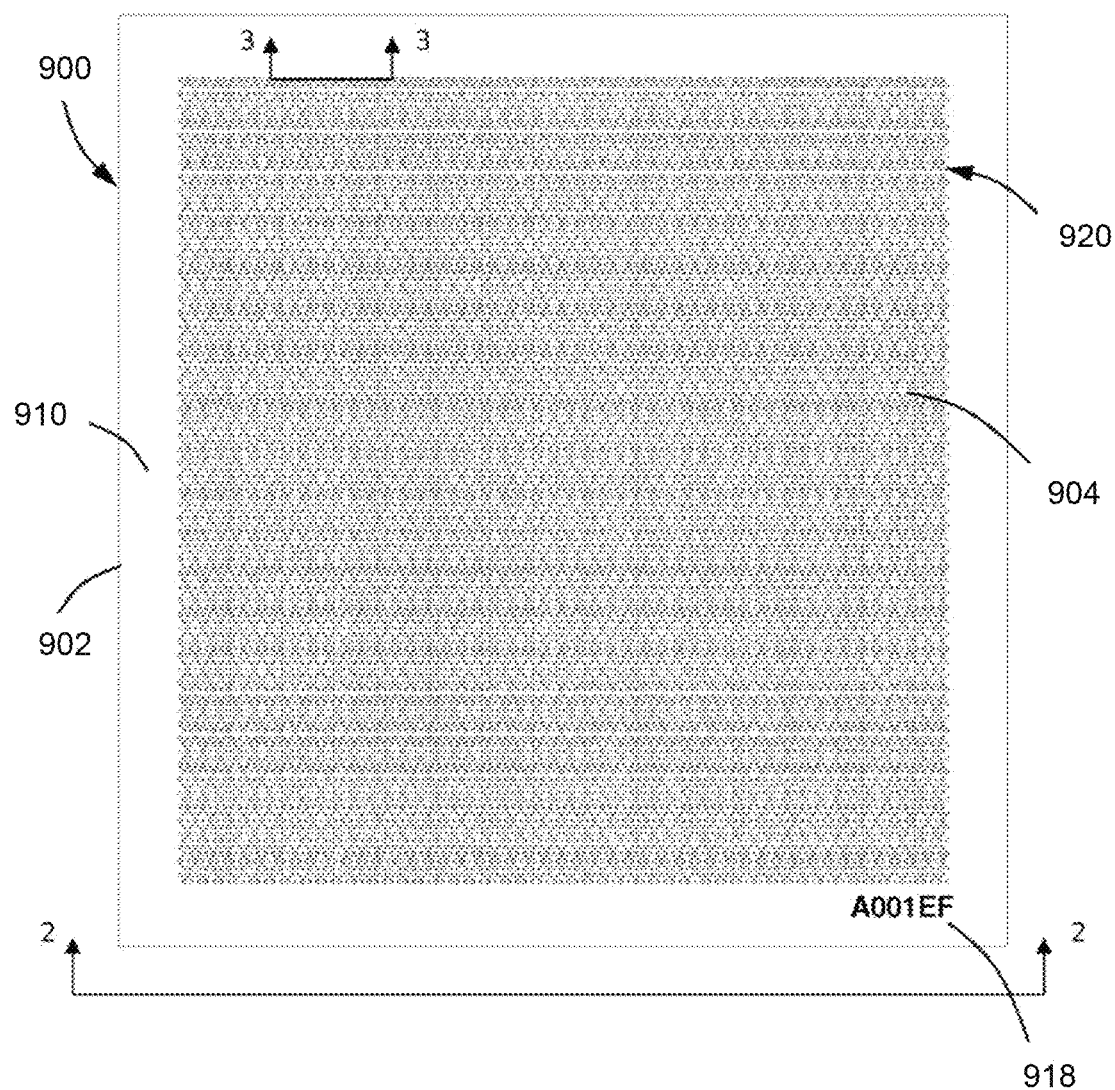
FIG. 9 illustrates a chip including a plurality of reaction sites in accordance with various embodiment described herein.

Referring to FIG. 9, in certain embodiments, a sample holder, an article, chip, device, substrate, slide, or plate 900 comprises a substrate 902 containing a plurality of reaction sites or reaction chambers 904 located in or on substrate 902. The plurality of reaction sites 904 may comprise a plurality of through-holes, wells, surface indentations, treated surface areas, or the like. In certain embodiments, sample holder 900 may comprise an article. Additionally or alternatively, sample holder 900 may comprise a microfluidic device which, for example, may further include a plurality of channels or paths for transferring reagents and/or test solutions to reaction sites 904. In other embodiments, reaction sites 904 comprise a plurality of droplets or beads and sample holder 900 may comprise one or more chambers and/or channels containing some or all of the droplets or beads 904. In such embodiments, the droplets or beads may form an emulsion, where some or all of the droplets or beads contain one or more target of at least one polynucleotide or nucleotide sequence. Where reaction sites 904 include beads, the beads may optionally include an attached optical signature or label. Droplets or beads may be inspected, monitored, or measured either one at time or in groups containing one or more droplets or beads, for example using an imaging system according to embodiments.

Reaction sites 904 may include reaction volumes located within through-holes, wells or indentations formed in substrate 902, spots of solution distributed on the surface 910, or other types of reaction chambers or formats, such as samples or solutions located within test sites or volumes of a microfluidic system, or within or on small beads or spheres.

Reaction sites 904 may be configured to provide sufficient surface tension by capillary action to draw in respective amounts of liquid or sample containing a biological components of interest. Sample holder 900 may have a general form or construction as disclosed in any of USPN's 6,306,578; 7,332,271; 7,604,983; 7,6825,65; 6,387,331; or 6,893,877, which are herein incorporated by reference in their entirety as if fully set forth herein. Substrate 902 may be a flat plate or comprise any form suitable for a particular application, assay, or experiment. Substrate 602 may comprise any of the various materials known in the fabrication arts including, but not limited to, a metal, glass, ceramic, silicon, or the like. Additionally or alternatively, substrate 902 may comprise a polymer material such as an acrylic, styrene, polyethylene, polycarbonate, and polypropylene material. Substrate 902 and reaction sites 904 may be formed by one or more of machining, injection molding, hot embossing, laser drilling, photolithography, or the like.

According to various embodiments of the present teachings, each reaction site 904 may have a volume of about 1.3 nanoliters. Alternatively, the volume of each reaction site may be less than 1.3 nanoliters. This may be achieved, for example, by decreasing the diameter of reaction site 904 and/or the thickness of the sample holder. For example, each reaction chamber 904 may have a volume that is less than or equal to 1 nanoliter, less than or equal to 100 picoliters, less than or equal to 30 picoliters, or less than or equal to 10 picoliters. In other embodiments, the volume some or all of the reaction sites 904 is in a range of 1 to 20 nanoliters.

In some embodiments, the reaction sites 904 are through-holes. In these examples, each through-hole has a volume of about 1.3 nanoliters. Alternatively, the volume each through-hole may be less than 1.3 nanoliters. This may be achieved, for example, by decreasing the diameter of through-hole and/or the thickness of the sample holder. For example, each through-hole may have a volume that is less than or equal to 1 nanoliter, less than or equal to 100 picoliters, less than or equal to 30 picoliters, or less than or equal to 10 picoliters. In other embodiments, the volume some or all of the through-holes is in a range of 1 to 20 nanoliters.

In various embodiments, a density of reaction sites 904 may be at least 100 reaction sites per square millimeter. In other embodiments, there may be higher densities of reaction chambers. For example, a density of reaction sites 904 within chip 100 may be greater than or equal to 150 reaction sites per square millimeter, greater than or equal to 200 reaction sites per square millimeter, greater than or equal to 500 reaction sites per square millimeter, greater than or equal to 1,000 reaction sites per square millimeter, greater than or equal to 10,000 reaction sites per square millimeter.

In some embodiments, the reaction sites 904 comprise a plurality of through-holes. Accordingly, a density of through-holes within a sample holder may be greater than or equal to 150 through-holes per square millimeter, greater than or equal to 200 through-holes per square millimeter, greater than or equal to 500 through-holes per square millimeter, greater than or equal to 1,000 through-holes per square millimeter, greater than or equal to 10,000 through-holes per square millimeter.

In some embodiments, reaction volumes may be segregated using through-holes, wells, or droplets. An exemplary volume range for reaction volumes is 1 aL to 50 uL. In other embodiments, the reaction volumes may be approximately 1 nL, 1 pL, 33 nL, or any other suitable volume.

In certain embodiments, surface 910 may comprise a hydrophobic material, for example, as described in US Patent Application Publication Numbers 2006/0057209 or 2006/0105453, which are herein incorporated by reference in their entirety as if fully set forth herein. In such embodiments, reaction sites 904 may comprise a hydrophilic material that attracts water or other liquid solutions. An array of such hydrophilic regions may comprise hydrophilic islands on a hydrophobic surface and may be formed on or within substrate 902 using any of various micro-fabrication techniques including, but are not limited to, depositions, plasmas, masking methods, transfer printing, screen printing, spotting, or the like.

Sample holder 900 may also include an identifier 918. In this example, identifier 918 may be an alpha-numeric sequence. However, it should be recognized that an identifier may be another type of symbol or characters according to various embodiments described herein. Identifier 918 may be, for example, a barcode, a QR code, a symbol, a numeric sequence, an RFID identifier, or an alpha sequence. Furthermore, although identifier 918 is shown in the bottom right corner of sample holder 900, identifier 918 may be located in any position on the sample holder as long as the position is known and stored in memory of the system according to various embodiments described herein.

FIG. 10 is a block diagram that illustrates the computer system 1000. Instruments (e.g., the system or instrument 10 shown in FIG. 1A and discussed above herein) to perform experiments may be connected to the exemplary computing system 1000. According to various embodiments, the instruments describer with reference to FIGS. 9 and 11 may utilized with computing system 1000. Computing system 1000 can include one or more processors, such as a processor 1004. Processor 1004 can be implemented using a general or special purpose processing engine such as, for example, a microprocessor, controller or other control logic. In this example, processor 1004 is connected to a bus 1002 or other communication medium.

Computing system 1000 may include bus 1002 or other communication mechanism for communicating information, and processor 1004 coupled with bus 1002 for processing information.

Computing system 1000 also includes a memory 1006, which can be a random access memory (RAM) or other dynamic memory, coupled to bus 1002 for storing instructions to be executed by processor 1004. Memory 1006 also may be used for storing temporary variables or other intermediate information during execution of instructions to be executed by processor 1004. Computing system 1000 may further include a read only memory (ROM) 1008 or other static storage device coupled to bus 1002 for storing static information and instructions for processor 1004.

Computing system 1000 may also include a storage device 1010, such as a magnetic disk, optical disk, or solid state drive (SSD) is provided and coupled to bus 1002 for storing information and instructions. Storage device 1010 may include a media drive and a removable storage interface. A media drive may include a drive or other mechanism to support fixed or removable storage media, such as a hard disk drive, a floppy disk drive, a magnetic tape drive, an optical disk drive, a CD or DVD drive (R or RW), flash drive, or other removable or fixed media drive. As these examples illustrate, the storage media may include a computer-readable storage medium having stored therein particular computer software, instructions, or data.

In alternative embodiments, storage device 1010 may include other similar instrumentalities for allowing computer programs or other instructions or data to be loaded into computing system 1000. Such instrumentalities may include, for example, a removable storage unit and an interface, such as a program cartridge and cartridge interface, a removable memory (for example, a flash memory or other removable memory module) and memory slot, and other removable storage units and interfaces that allow software and data to be transferred from the storage device 1010 to computing system 1000.

Computing system 1000 can also include a communications interface 1018. Communications interface 1018 can be used to allow software and data to be transferred between computing system 1000 and external devices. Examples of communications interface 1018 can include a modem, a network interface (such as an Ethernet or other NIC card), a communications port (such as for example, a USB port, a RS-232C serial port), a PCMCIA slot and card, Bluetooth, etc. Software and data transferred via communications interface 1018 are in the form of signals which can be electronic, electromagnetic, optical or other signals capable of being received by communications interface 1018. These signals may be transmitted and received by communications interface 1018 via a channel such as a wireless medium, wire or cable, fiber optics, or other communications medium. Some examples of a channel include a phone line, a cellular phone link, an RF link, a network interface, a local or wide area network, and other communications channels.

Computing system 1000 may be coupled via bus 1002 to a display 1012, such as a cathode ray tube (CRT) or liquid crystal display (LCD), for displaying information to a computer user. An input device 1014, including alphanumeric and other keys, is coupled to bus 1002 for communicating information and command selections to processor 1004, for example. An input device may also be a display, such as an LCD display, configured with touchscreen input capabilities.

Figure 11:
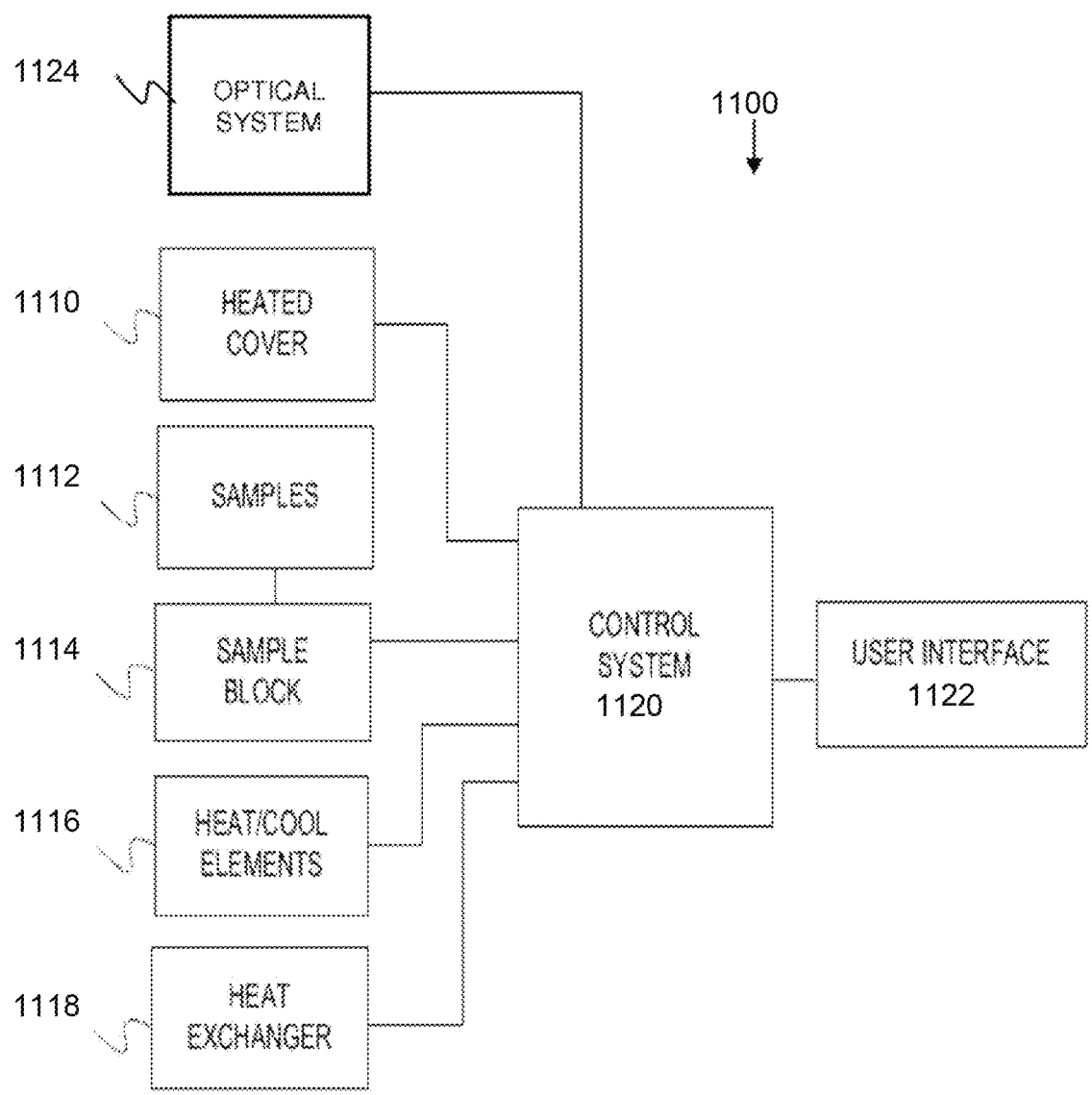
FIG. 11 illustrates a block diagram of exemplary instruments in accordance with various embodiments described herein.

It will be appreciated that, for clarity purposes, the above description has described embodiments with reference to different functional units and processors. However, it will be apparent that any suitable distribution of functionality between different functional units, processors or domains may be used without detracting from the disclosure. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization. As mentioned above, an instrument that may be utilized according to various embodiments, but is not limited to, is a polymerase chain reaction (PCR) instrument. FIG. 11 is a block diagram that illustrates an amplification instrument 1100, upon which embodiments of the present teachings may be implemented. Amplification instrument 1100 may include a heated cover 1110 that is placed over a plurality of samples 1112 contained in chip or a consumable, for example. In various embodiments, a consumable may be a glass or plastic slide with a plurality of sample regions, which sample regions have a cover between the sample regions and heated cover 1110. Some examples of a consumable may include, but are not limited to, a multi-well plate, such as a standard microtiter 96-well, a 384-well plate, or a microcard, or a substantially planar support, such as a glass or plastic slide. The reaction sites in various embodiments of a consumable may include depressions, indentations, ridges, and combinations thereof, patterned in regular or irregular arrays formed on the surface of the consumable. Various embodiments of amplification instruments include a sample block 1114, elements for heating and cooling 1116, a heat exchanger 1118, control system 1120, and user interface 1122. Various embodiments of a thermal block assembly according to the present teachings comprise components 1114-1118 of amplification instrument 1100 of FIG. 11.

Real-time amplification instrument 1100 has an optical system 1124. In FIG. 11, an optical system 1124 may have an illumination source (not shown) that emits electromagnetic energy, an optical sensor, detector, or imager (not shown), for receiving electromagnetic energy from samples 1112 in a consumable, and optics 1140 used to guide the electromagnetic energy from each DNA sample to the imager. For embodiments of amplification instrument 1100 in FIG. 11 and real-time amplification instrument 1100 in FIG. 11, control system 1120, may be used to control the functions of the detection system, heated cover, and thermal block assembly. Control system 1120 may be accessible to an end user through user interface 1122 of amplification instrument 1100 in FIG. 8 and real-time amplification instrument 1100 in FIG. 11. Also a computer system 1000, as depicted in FIG. 10, may serve as to provide the control the function of amplification instrument 1100 in FIG. 11, as well as the user interface function. Additionally, computer system 1000 of FIG. 10 may provide data processing, display and report preparation functions. Such instrument control functions may be dedicated locally to the amplification instrument, or computer system 1000 of FIG. 10 may provide remote control of part or all of the control, analysis, and reporting functions, as will be discussed in more detail subsequently.

As an alternative to low reaction volume chambers as described above for carrying out nucleic acid amplification monitoring in a stationary sample, the sample may be caused to flow through a channel or chamber of a microfluidic device and as it flows it may be subjected consecutively to different temperatures whereby thermo-cycling is achieved. Thus, for example, the sample may be caused to flow through a channel or chamber which passes consecutively through different temperature zones suitable for the amplification stages of denaturing, primer annealing and primer extension, e.g. a channel in a microfluidic device, such as, for example, a silicon chip device, which passes consecutively through zones of different temperature provided in the base suitable for successive repeats along the channel of the stages of denaturing, primer annealing and primer extension. Such microfluidic structures for performing continuous flow nucleic acid amplification on a chip are described, for example, in Auroux et al., Minaturised Nucleic Acid Analysis Lab Chip (2004) 4, 534-546. Structures of this type may be fabricated through the use of standard microfabrication techniques using for example photolithography to define the fluidic network and then an etching or deposition step to create the required channel or channels, for example in a PMMA, acrylic, Perspex™ or glass substrate. A cover plate in glass or PMMA or other material may or may not be overlaid to cover the channels. The base of the channel or channels may be formed by substrate bonding to a silicon chip and temperature sensors as well as heating or heat pump (Peltier) elements, such that the reaction mixture is in direct contact with these sensors and actuators, and may or may not include circuitry for temperature control.

Alternatively, the base of the channel(s) may be formed by a printed circuit board (PCB) housing temperature sensors such that these are in direct contact with the reaction mixture. The PCB may also house heating or heat pump elements, sensor interface and temperature control circuitry. Reagents present within the microfluidic channel or chamber may be those of the buffered amplification reaction mixture, which may include the primers chosen for ability to hybridize to the target at sites suitable for amplification of the chosen sequence, the required enzyme or enzymes for amplification and all four dNTPs in excess.

Temperature control may be achieved by a proportional-integral-derivative (PID) controller, which is one of the most common closed-loop feedback control systems. Errors between the measured temperature and the target temperature may be then used to calculate the level of heating required. Calculation of this output level may be performed based on the current error directly (proportional), the history of the error (integral), and the predicted future error based on its rate of change (derivative). Similarly, a PI controller may stabilize temperature based on present and historical values of the error as described in Iordanov et al. (2004) ibid. Alternatively, techniques such as pulse-width modulation or duty-cycling may be implemented.

It may alternatively be chosen to have a reciprocating system whereby the amplification mixture is moved backwards and forwards in a microchamber between the required temperature zones for thermo-cycling. As an alternative to contact heating for thermo-cycling, various noncontact heating methods may be employed as also discussed in the same review article, including by way of example hot-air mediated heating, utilization of IR light, laser-mediated heating, induction heating and microwave irradiation.

In an embodiment, a flow based melt may similarly be performed. For example, a sample comprising amplified product may be disposed to flow along an axis of a temperature gradient and monitored by a detector, such as a fluorescence detector. As described herein, changes to indicators of amplification (e.g., fluorescence), may be detected as the sample flows over the temperature gradient. Based on the location of the sample along the gradient and the known temperature conditions along the gradient, detected changes in the indicators of amplification may be associated with a particular melt temperature (or temperature window). The sample may be flowed using devices, such as a chip or circuit board, and channels, as described herein with reference to flow based PCR amplification. The temperature gradient may be achieved using one or more heater, as described herein with reference to the flow based PCR amplification.

In various exemplary embodiments in accordance with the present disclosure, digital nucleic acid amplification (e.g., dPCR) may be performed using a microfabricated chip that includes an array of reaction sites or chambers into which the sample is segregated into separate reaction volumes (sample portions) upon being introduced to the device. In such a device, the sample portions remain in their individual reaction sites or chambers while subjected to the amplification assay, including for example the various stages of thermal cycling.

In other embodiments, reaction volumes may be segregated using droplets. For example, a plurality of droplets may be generated using a device, for instance, by drawing a sample and oil through a nozzle. The droplets may be approximately 1 nL in an embodiment. The droplets may then be transferred for thermal cycling such that PCR amplification may be achieved. For example, the droplets may be transferred to a PCR plate or a chip with reaction sites or chambers, and a thermal cycler may be used to cycle the droplets through phases of amplification. The droplets may then be exposed to a reader in order to determine amplification results. For instance, the PCR plate or chip may be loaded onto a reader that draws the droplets from each reaction site or chamber and exposes them to a reader (such as a detector that measures fluorescence).

In another embodiment, after generation of the droplets, a flow based technique may be used to perform thermal cycling. For example, the droplets may be caused to flow through a channel or chamber which passes consecutively through different temperature zones suitable for the amplification stages of denaturing, primer annealing and primer extension, e.g. a channel in a microfluidic device, such as, for example, a silicon chip device, which passes consecutively through zones of different temperature provided in the base suitable for successive repeats along the channel of the stages of denaturing, primer annealing and primer extension. Similarly, the droplets may then be exposed to a reader in order to determine amplification results.

In order to perform the described melt analysis, the droplets may be loaded on to a device, such as a plate or a chip, and a heater may be used to systematically heat the droplets, as described herein with reference to melt performance on a segregated sample within reaction sites or chambers. In another embodiment, the droplets may be caused to flow down a temperature gradient while also being exposed to a detector, such as a fluorescence detector, as described herein with reference to the flow based melt performance embodiment. In such a configuration, known temperatures may be associated with locations along the gradient, and the location at which indicators of amplification change (e.g., decrease) along the gradient may be used to determine a melt temperature.

Those skilled in the art will appreciate that the features described above can be combined in various ways to form multiple variations of exemplary embodiments in accordance with the present disclosure, and that various modifications may be made to the configuration and methodology of the exemplary embodiments disclosed herein without departing from the scope of the present disclosure and claims. Those skilled in the art also will appreciate that various features disclosed with respect to one exemplary embodiment herein may be used in combination with other exemplary embodiments with appropriate modifications, even if such combinations are not explicitly disclosed herein.

What is claimed is:

1. A method of analysis for detecting and/or quantifying a nucleic acid in a sample, the method comprising:
    within a plurality of sample reaction volumes, segregating a sample comprising a target nucleic acid associated with a first indicator of amplification, wherein the plurality of sample reaction volumes includes a first plurality of the sample reaction volumes each containing at least one molecule of the target nucleic acid, and a second plurality of the sample reaction volumes each containing no molecules of the target nucleic acid;
    subjecting the first and second pluralities of sample reaction volumes to an amplification assay, wherein the amplification assay is configured to amplify the target nucleic acid to produce an amplified product of the target nucleic acid;
    during the subjecting, taking a plurality of measurements of the first indicator of amplification for each of the first plurality of sample reaction volumes;
    after taking the plurality of measurements, taking a post amplification assay measurement of the first indicator for each of the first plurality of sample reaction volumes;
    determining that some of the first plurality of sample reaction volumes contain an amount of the amplified product based on the post amplification assay;
    determining that the post amplification assay measurement of at least one of the first plurality of sample reaction volumes is not consistent with a sample reaction volume containing the amplified product;
    determining an angle of launch of the at least one of the first plurality of sample reaction volumes based on at least two of the plurality of measurements of the first indicator of amplification;
    determining that the at least one of the first plurality of sample reaction volumes contains an amount of the amplified product based angle of launch.

2. The method of claim 1, further comprising:
    taking at least a first and second post-amplification measurement of the first indicator of amplification at a first and second temperature, respectively, for at least one of the first plurality of sample reaction volumes;
    identifying one or more changes in the first indicator of amplification based on the post-amplification measurements of the first indicator or amplification;
    associating the at least one change to a post-amplification temperature;
    comparing the post-amplification temperature associated with the at least one change to an expected melt temperature for the target nucleic acid; and
    identifying an erroneous amplification product based on the comparing.

3. The method of claim 2, wherein taking a plurality of measurements of the first indicator of amplification further comprises:
    associating the measurements of the first indicator of amplification for the first plurality of sample reaction volumes to a quantification cycle value ($C_q$);
    comparing the quantification cycle values associated with the plurality of measurements to an expected quantification cycle value for the amplification assay; and identifying an erroneous amplification product based on the comparing.

4. A system for detecting or quantifying a nucleic acid in a sample, the system comprising:
- a reaction device;
- an electronic processor;
- a memory comprising instructions for performing the method of claim 1;
- an input/output device comprising an input device and a display;
- wherein the electronic processor performs the instructions and displays an amount of one or more target nucleic acids on the display or wherein the electronic processor performs the instructions and displays information regarding a detection of one or more target nucleic acids on the display.

5. The method of claim 1, further comprising quantifying the amplification, wherein quantifying the amplification comprises determining a quantification cycle value ($C_g$) or a cycle threshold value based on the detecting or measuring the first indicator of amplification, wherein the cycle threshold value is a value at which the measured indicator of amplification reaches a predetermined threshold value.

\* \* \* \* \*